(12) United States Patent
Rogers et al.

(10) Patent No.: US 11,235,124 B2
(45) Date of Patent: *Feb. 1, 2022

(54) COLLAPSIBLE CATHETER AND METHOD FOR CALCULATING FRACTIONAL FLOW RESERVE

(71) Applicant: Medtronic Vascular, Inc., Santa Rosa, CA (US)

(72) Inventors: Ronan Rogers, Galway (IE); Matthew Fleming, Roscommon (IE); Barry O'Connell, Galway (IE); Timothy Jones, Galway (IE); Joshua Hillas, Galway (IE); David Callanan, Ballybrit (IE); Michael Takaza, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 812 days.

This patent is subject to a terminal disclaimer.

(21) Appl. No.: 15/672,792

(22) Filed: Aug. 9, 2017

(65) Prior Publication Data

US 2019/0046762 A1  Feb. 14, 2019

(51) Int. Cl.
*A61M 25/00* (2006.01)
*A61B 5/00* (2006.01)
*A61B 5/02* (2006.01)
*A61B 5/0215* (2006.01)
*A61M 25/10* (2013.01)
*A61M 25/01* (2006.01)

(52) U.S. Cl.
CPC .......... *A61M 25/0023* (2013.01); *A61B 5/00* (2013.01); *A61B 5/02007* (2013.01); *A61B 5/0215* (2013.01); *A61B 5/6876* (2013.01); *A61M 25/007* (2013.01); *A61M 25/0075* (2013.01); *A61M 25/0052* (2013.01); *A61M 25/10184* (2013.11); *A61M 2025/0002* (2013.01); *A61M 2025/0024* (2013.01); *A61M 2025/0177* (2013.01); *A61M 2025/0183* (2013.01)

(58) Field of Classification Search
None
See application file for complete search history.

(56) References Cited

U.S. PATENT DOCUMENTS 4,406,656 A * 9/1983 Hattler .............. A61M 25/0009
                                                604/103.14
4,601,713 A * 7/1986 Fuqua ............... A61M 25/0023
                                                604/103.14

(Continued)

FOREIGN PATENT DOCUMENTS

DE  10 2008 045878 A1   3/2010
EP       0263190        10/1986

(Continued)

*Primary Examiner* — Michael R Bloch

(57) ABSTRACT

A catheter for measuring a fractional flow reserve includes a proximal shaft, a distal shaft coupled to a distal portion of the proximal shaft, and a pressure sensor coupled to the distal shaft. The proximal shaft includes a distal portion configured to extend through a stenosis in a vessel. The distal portion of the proximal shaft includes a radially expanded configuration having a first diameter and a radially collapsed configuration having a second diameter, wherein the first diameter is larger than the second diameter. The distal shaft includes a guidewire lumen configured to receive therein.

17 Claims, 21 Drawing Sheets

(56) References Cited

U.S. PATENT DOCUMENTS

| | | | |
|---|---|---|---|
| 4,718,425 A | 1/1988 | Tanaka et al. | |
| 4,771,782 A | 9/1988 | Millar | |
| 4,796,641 A | 1/1989 | Mills et al. | |
| 4,815,472 A | 3/1989 | Wise et al. | |
| 4,850,358 A | 7/1989 | Millar | |
| 4,901,731 A | 2/1990 | Millar | |
| 4,924,877 A | 5/1990 | Brooks | |
| 4,928,693 A | 5/1990 | Goodin et al. | |
| 4,936,310 A | 6/1990 | Engstrom et al. | |
| 4,941,473 A | 7/1990 | Tenerz et al. | |
| 4,966,148 A | 10/1990 | Millar | |
| 4,966,156 A | 10/1990 | Perry et al. | |
| 5,029,585 A | 7/1991 | Lieber et al. | |
| 5,046,497 A | 9/1991 | Millar | |
| 5,050,297 A | 9/1991 | Metzger | |
| 5,085,223 A | 2/1992 | Lars et al. | |
| 5,106,368 A * | 4/1992 | Uldall | A61M 25/003 604/178 |
| 5,125,058 A | 6/1992 | Tenerz et al. | |
| 5,195,375 A | 3/1993 | Tenerz et al. | |
| 5,267,958 A | 12/1993 | Buchbinder et al. | |
| 5,280,786 A | 1/1994 | Wlodarczyk et al. | |
| 5,318,588 A * | 6/1994 | Horzewski | A61M 25/0023 604/104 |
| 5,427,114 A | 6/1995 | Colliver et al. | |
| 5,451,233 A | 9/1995 | Yock | |
| 5,466,222 A | 11/1995 | Ressemann et al. | |
| 5,472,418 A * | 12/1995 | Palestrant | A61M 25/0021 604/264 |
| 5,526,820 A | 6/1996 | Khoury | |
| 5,542,434 A | 8/1996 | Imran et al. | |
| 5,564,425 A | 10/1996 | Tonokura | |
| 5,569,219 A | 10/1996 | Hakki et al. | |
| 5,573,007 A | 11/1996 | Bobo, Sr. | |
| 5,591,129 A | 1/1997 | Shoup et al. | |
| 5,637,091 A | 6/1997 | Hakky et al. | |
| RE35,648 E | 11/1997 | Tenerz et al. | |
| 5,694,946 A | 12/1997 | Tenerz et al. | |
| 5,701,905 A | 12/1997 | Esch | |
| 5,715,827 A | 2/1998 | Corl et al. | |
| 5,738,901 A * | 4/1998 | Wang | A61M 25/0045 427/2.12 |
| 5,813,997 A | 9/1998 | Imran et al. | |
| 5,827,243 A | 10/1998 | Palestrant | |
| 5,873,835 A | 2/1999 | Hastings et al. | |
| 5,902,248 A | 5/1999 | Millar et al. | |
| 5,964,714 A | 10/1999 | Lafontaine | |
| 5,997,508 A | 12/1999 | Lunn et al. | |
| 6,033,366 A | 3/2000 | Brockway et al. | |
| 6,056,719 A * | 5/2000 | Mickley | A61M 25/104 604/96.01 |
| 6,089,103 A | 7/2000 | Smith | |
| 6,106,476 A | 8/2000 | Corl et al. | |
| 6,106,486 A | 8/2000 | Tenerz et al. | |
| 6,112,598 A | 9/2000 | Tenerz et al. | |
| 6,142,958 A | 11/2000 | Hammarstrom et al. | |
| 6,167,763 B1 | 1/2001 | Tenerz et al. | |
| 6,179,856 B1 | 1/2001 | Barbere | |
| 6,182,513 B1 | 2/2001 | Stemme et al. | |
| 6,193,669 B1 | 2/2001 | Degany et al. | |
| 6,224,585 B1 | 5/2001 | Pfeiffer | |
| 6,248,083 B1 | 6/2001 | Smith et al. | |
| 6,295,990 B1 * | 10/2001 | Lewis | A61B 17/22 128/898 |
| 6,296,615 B1 | 10/2001 | Brockway et al. | |
| 6,312,380 B1 | 11/2001 | Hoek et al. | |
| 6,336,906 B1 | 1/2002 | Hammarstrom et al. | |
| 6,354,999 B1 | 3/2002 | Dgany et al. | |
| 6,379,308 B1 | 4/2002 | Brockway et al. | |
| 6,394,986 B1 | 5/2002 | Millar | |
| 6,409,677 B1 | 6/2002 | Tulkki | |
| 6,471,656 B1 | 10/2002 | Shalman et al. | |
| 6,517,481 B2 | 2/2003 | Hoek et al. | |
| 6,546,804 B2 | 4/2003 | Stemme et al. | |
| 6,551,250 B2 | 4/2003 | Khalil | |
| 6,565,514 B2 | 5/2003 | Svanerudh et al. | |
| 6,585,660 B2 | 7/2003 | Dorando et al. | |
| 6,615,667 B2 | 9/2003 | Smith | |
| 6,659,957 B1 | 12/2003 | Vardi et al. | |
| 6,659,959 B2 | 12/2003 | Brockway et al. | |
| 6,663,570 B2 | 12/2003 | Mott et al. | |
| 6,716,178 B1 | 4/2004 | Kilpatrick et al. | |
| 6,733,459 B1 | 5/2004 | Atsumi | |
| 6,754,608 B2 | 6/2004 | Svanerudh et al. | |
| 6,767,327 B1 | 7/2004 | Corl et al. | |
| 6,821,287 B1 | 11/2004 | Jang | |
| 6,860,851 B2 | 3/2005 | Knudson | |
| 6,868,736 B2 | 3/2005 | Sawatari et al. | |
| 6,926,674 B2 | 8/2005 | Tenerz et al. | |
| 6,938,474 B2 | 9/2005 | Melvangs | |
| 6,966,890 B2 | 11/2005 | Coyle et al. | |
| 6,974,422 B1 | 12/2005 | Millar | |
| 6,976,965 B2 | 12/2005 | Corl et al. | |
| 6,993,974 B2 | 2/2006 | Tenerz et al. | |
| 6,994,695 B1 | 2/2006 | Millar | |
| 7,017,416 B1 | 3/2006 | Liu et al. | |
| 7,021,152 B2 | 4/2006 | Tenerz | |
| 7,025,727 B2 | 4/2006 | Brockway et al. | |
| 7,060,038 B2 | 6/2006 | Letort et al. | |
| 7,097,620 B2 | 8/2006 | Corl et al. | |
| 7,112,170 B2 | 9/2006 | Schock et al. | |
| 7,134,994 B2 | 11/2006 | Alpert et al. | |
| 7,137,953 B2 | 11/2006 | Eigler et al. | |
| 7,211,048 B1 | 5/2007 | Najafi et al. | |
| 7,222,539 B2 | 5/2007 | Tulkki | |
| 7,229,403 B2 | 6/2007 | Schock et al. | |
| 7,245,789 B2 | 7/2007 | Bates et al. | |
| 7,263,894 B2 | 9/2007 | Tenerz | |
| 7,274,956 B2 | 9/2007 | Mott et al. | |
| RE39,863 E | 10/2007 | Smith | |
| 7,294,117 B2 | 11/2007 | Provost-tine et al. | |
| 7,329,223 B1 | 2/2008 | Ainsworth et al. | |
| 7,331,236 B2 | 2/2008 | Smith et al. | |
| 7,343,811 B2 | 3/2008 | Tenerz et al. | |
| 7,347,822 B2 | 3/2008 | Brockway et al. | |
| 7,447,388 B2 | 11/2008 | Bates et al. | |
| 7,450,989 B2 | 11/2008 | Svanerudh | |
| 7,454,244 B2 | 11/2008 | Kassab et al. | |
| 7,458,938 B2 | 12/2008 | Patel et al. | |
| 7,472,601 B1 | 1/2009 | Tenerz et al. | |
| 7,481,774 B2 | 1/2009 | Brockway et al. | |
| 7,527,594 B2 | 5/2009 | Vardi et al. | |
| 7,532,920 B1 | 5/2009 | Ainsworth et al. | |
| 7,599,588 B2 | 10/2009 | Eberle et al. | |
| 7,645,233 B2 | 1/2010 | Tulkki et al. | |
| 7,660,492 B2 | 2/2010 | Bates et al. | |
| 7,724,148 B2 | 5/2010 | Samuelsson et al. | |
| 7,731,664 B1 | 6/2010 | Millar | |
| 7,775,988 B2 | 8/2010 | Pijls | |
| 7,783,338 B2 | 8/2010 | Ainsworth et al. | |
| 7,837,650 B1 | 11/2010 | Cox et al. | |
| 7,881,573 B2 | 2/2011 | Eberle et al. | |
| 7,931,603 B2 | 4/2011 | Von Malmborg et al. | |
| 7,946,997 B2 | 5/2011 | Hubinette | |
| 7,967,761 B2 | 6/2011 | Smith | |
| 7,967,762 B2 | 6/2011 | Corl et al. | |
| 7,998,089 B2 | 8/2011 | Smith | |
| 8,025,623 B1 | 9/2011 | Millar | |
| 8,029,447 B2 | 10/2011 | Kanz et al. | |
| 8,059,923 B2 | 11/2011 | Bates et al. | |
| 8,140,146 B2 | 3/2012 | Kim et al. | |
| 8,157,742 B2 | 4/2012 | Taylor | |
| 8,162,856 B2 | 4/2012 | Williams et al. | |
| 8,174,395 B2 | 5/2012 | Samuelsson et al. | |
| 8,187,195 B2 | 5/2012 | Tulkki | |
| 8,216,151 B2 | 7/2012 | Smith | |
| 8,231,537 B2 | 7/2012 | Ahmed et al. | |
| 8,249,815 B2 | 8/2012 | Taylor | |
| 8,277,386 B2 | 10/2012 | Ahmed et al. | |
| 8,282,565 B2 | 10/2012 | Mahapatra et al. | |
| 8,298,156 B2 | 10/2012 | Manstrom et al. | |
| 8,311,747 B2 | 11/2012 | Taylor | |
| 8,311,748 B2 | 11/2012 | Taylor et al. | |

(56) References Cited

U.S. PATENT DOCUMENTS

| | | |
|---|---|---|
| 8,311,750 B2 | 11/2012 | Taylor |
| 8,315,812 B2 | 11/2012 | Taylor |
| 8,315,813 B2 | 11/2012 | Taylor et al. |
| 8,315,814 B2 | 11/2012 | Taylor et al. |
| 8,317,715 B2 | 11/2012 | Belleville et al. |
| 8,320,723 B2 | 11/2012 | Eberle et al. |
| 8,321,150 B2 | 11/2012 | Taylor |
| 8,410,940 B2 | 4/2013 | Samuelsson et al. |
| 8,419,647 B2 | 4/2013 | Corl et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,556,520 B2 | 10/2013 | Elenbaas et al. |
| 8,562,537 B2 | 10/2013 | Alpert et al. |
| 8,636,659 B2 | 1/2014 | Alpert et al. |
| 8,696,584 B2 | 4/2014 | Kassab |
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan et al. |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0184105 A1 | 8/2006 | Townsend et al. |
| 2006/0207335 A1 | 9/2006 | Tenerz et al. |
| 2006/0235458 A1* | 10/2006 | Belson ............ A61M 25/0032 606/191 |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith et al. |
| 2008/0077085 A1 | 3/2008 | Eidenschink et al. |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Naghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2009/0281394 A1 | 11/2009 | Russell et al. |
| 2010/0014810 A1 | 1/2010 | Eberle et al. |
| 2010/0087732 A1 | 4/2010 | Eberle et al. |
| 2010/0094392 A1 | 4/2010 | Nguyen et al. |
| 2010/0109104 A1 | 5/2010 | Tiensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn et al. |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1* | 7/2012 | Smith ................ A61B 5/0215 600/486 |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |

(56) References Cited

U.S. PATENT DOCUMENTS

| | | |
|---|---|---|
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0190633 A1 | 7/2013 | Dorando et al. |
| 2013/0216481 A1 | 8/2013 | Rosenmeier |
| 2013/0303914 A1 | 11/2013 | Hiltner et al. |
| 2013/0324864 A1 | 12/2013 | Manstrom et al. |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0121629 A1 | 5/2014 | Macaulay et al. |
| 2014/0180140 A1 | 6/2014 | Alpert |
| 2014/0180141 A1 | 6/2014 | Millett |
| 2014/0187980 A1 | 7/2014 | Burkett |
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0074995 A1 | 3/2015 | Patil et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0196210 A1 | 7/2015 | McCaffrey et al. |
| 2015/0223707 A1 | 8/2015 | Ludoph |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1 | 12/2015 | McCaffrey et al. |
| 2015/0359439 A1 | 12/2015 | Manstrom et al. |
| 2015/0360000 A1* | 12/2015 | Sansoucy .......... A61M 25/0102 264/154 |
| 2016/0022153 A1 | 1/2016 | Dorando |
| 2016/0066802 A1 | 3/2016 | Keller |
| 2016/0106321 A1 | 4/2016 | Sharma et al. |
| 2016/0199003 A1 | 7/2016 | McCaffrey et al. |

FOREIGN PATENT DOCUMENTS

| | | |
|---|---|---|
| EP | 1658808 | 8/1995 |
| EP | 1260175 | 11/2002 |
| EP | 1419796 | 5/2004 |
| EP | 1493381 | 1/2005 |
| EP | 1514512 | 3/2005 |
| EP | 1702641 | 9/2006 |
| JP | 2004-194996 A | 7/2004 |
| JP | 3638066 B2 | 4/2005 |
| JP | 3705458 B2 | 10/2005 |
| JP | 2006-204378 A | 8/2006 |
| NL | 2009285 | 8/2012 |
| WO | WO1997/000641 | 1/1997 |
| WO | WO1999/058059 | 11/1999 |
| WO | WO2003/022122 | 3/2003 |
| WO | WO2006/037082 | 4/2006 |
| WO | WO2006/117154 | 11/2006 |
| WO | WO2011/120565 | 10/2011 |
| WO | WO2011/161212 | 12/2011 |
| WO | WO2012/093260 | 7/2012 |
| WO | WO2012/173697 | 12/2012 |
| WO | WO2013/061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

* cited by examiner

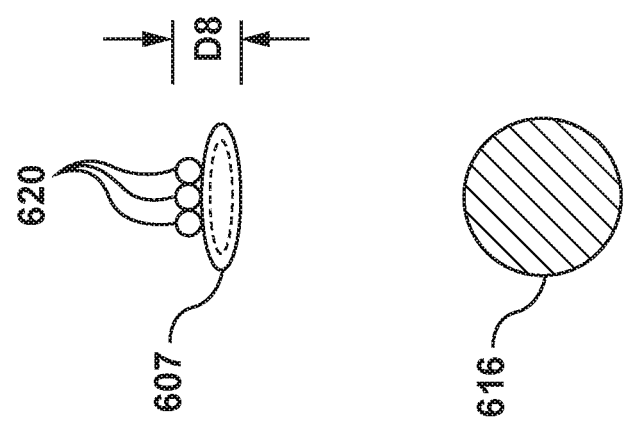
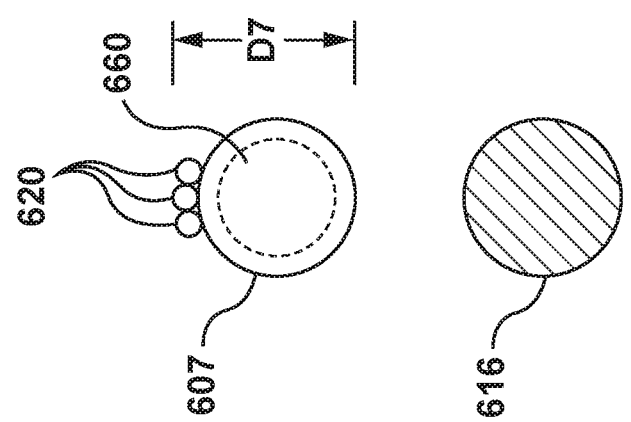

COLLAPSIBLE CATHETER AND METHOD FOR CALCULATING FRACTIONAL FLOW RESERVE

FIELD OF THE INVENTION

The present invention relates to systems and methods for calculating a Fractional Flow Reserve. More particularly, the present invention relates to a collapsible catheter for calculating a Fractional Flow Reserve.

BACKGROUND OF THE INVENTION

The severity of a stenosis or lesion in a blood vessel may be assessed by obtaining proximal and distal pressure measurements relative to the given stenosis and using those measurements for calculating a value of a Fractional Flow Reserve (FFR). FFR is defined as the ratio of a distal pressure $P_d$ measures on a distal side of the stenosis to a proximal pressure $P_a$ measured on a proximal side of the stenosis, typically within the aorta (FFR=$P_d/P_a$). Conventionally, a sensor is placed on a distal portion of a guidewire (FFR wire) to obtain/measure the distal pressure $P_d$, while an external pressure transducer is fluidly connected via tubing to a guide catheter for obtaining the proximal, or aortic (AO) pressure $P_a$. Once the guide catheter is positioned in situ, and the pressure of the blood filling the lumen of the guide catheter is equal to the pressure of the blood at the distal tip of the guide catheter, tubing that fluidly connects the proximal end of the guide catheter to the external pressure transducer also fills with blood such that the external pressure transducer measures the pressure of the blood at the distal tip of the guide catheter. The FFR wire is advanced through the guide catheter and through the lesion to a distal side of the lesion. The sensor on the FFR wire measures the distal pressure.

Calculation of the FFR value provides a stenosis specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation. If an interventional treatment is required, the interventional device, such as a balloon catheter, is tracked over a guidewire to the site of the stenosis. Conventional FFR wires generally are not desired by clinicians to be used as guidewires for such interventional devices. Accordingly, if an interventional treatment is required, the clinician generally removes the FFR wire, inserts a conventional guidewire, and tracks the interventional device to the treatment site over the conventional guidewire.

To address this concern, efforts have been made to utilize catheters to take pressure measurements for calculating FFR. Using a catheter (FFR catheter or micro-catheter), a clinician may use a preferred guidewire for tracking the FFR catheter to the site of the stenosis. If an interventional treatment is required, the FFR catheter may be removed while the guidewire used with the FFR catheter may remain in situ, and the interventional device may be tracked over the existing guidewire to the site of the stenosis.

However, such FFR catheters are generally larger in cross-sectional profile than FFR wires. Therefore, some error may be introduced into the measured proximal pressure $P_a$ and the measured distal pressure $P_d$, as compared to measurements taken using an FFR wire. In particular, an FFR catheter disposed over a guidewire occupies a larger percentage of the guide catheter lumen than a comparatively smaller profile FFR wire. Occupying a larger percentage of the guide catheter lumen may affect the accuracy of the measured proximal pressure $P_a$, which, as explained above, is based on blood filling the lumen of the guide catheter. This error is referred to as dampening of the AO pressure wave. Due to the reduced space between the inner surface of the guide catheter and an outer surface of the proximal portion of the FFR catheter/guidewire combination, the pressure at the distal end of the guide catheter does not propagate proximally through the guide catheter such that changes in the pressure at the distal end of the guide catheter are not properly measured by the external pressure transducer. Thus, using a larger profile FFR catheter may introduce errors in the measured proximal pressure ($P_a$). Such errors would then be transferred to the calculation of FFR, which is based in part on the measured proximal pressure.

Further, the lager cross-sectional profile of a distal portion of an FFR catheter, as compared to an FFR wire, occupies a larger percentage of the vessel distal of the guide catheter and across the stenosis. Occupying a larger percentage of the vessel affects the fluid dynamics of the blood flow through the stenosis, thereby causing the measured distal pressure $P_d$ to deviate from distal pressure of the same vessel and same stenosis measured with a conventional FFR wire. Deviation of the measured distal pressure $P_d$ is transferred to the calculated FFR.

Thus, using an FFR catheter may cause the calculated FFR to deviate from FFR calculated using measurements taken with an FFR wire. Because interventional decisions have been made based on FFR measured using FFR wires, this may lead to "false positives" or "false negatives". A "false positive" is where the FFR calculated using measurements taken with an FFR catheter is lower than the threshold for intervention (e.g. below 0.80) but if the FFR were calculated using measurements taken with an FFR wire, the FFR would have been higher than the threshold (e.g. above 0.80). A "false negative" is where the FFR calculated using measurements taken with an FFR catheter is higher than the threshold for intervention (e.g. above 0.80) but if the FFR were calculated using measurements taken with an FFR wire, the FFR would have been lower than the threshold (e.g. below 0.80).

Accordingly, there is a need to reduce the cross-sectional profile of FFR catheters to minimize deviation of FFR calculated using an FFR catheter as compared to FFR calculated using an FFR guidewire.

BRIEF SUMMARY OF THE INVENTION

Embodiments hereof relate to a catheter for measuring a fractional flow reserve including a proximal shaft, a distal shaft, a pressure sensor, and at least one pressure sensor wire. The proximal shaft includes a radially expanded configuration and a radially collapsed configuration. The proximal shaft has a first outer diameter in the radially expanded configuration and a second outer diameter in the radially collapsed configuration. The distal shaft defines a guidewire lumen configured to receive a guidewire. The pressure sensor is coupled to the distal shaft. The at least one pressure sensor wire is operably connected to the pressure sensor and extends proximally from the pressure sensor within a distal shaft wall of the distal shaft and into a proximal shaft wall of proximal shaft.

Embodiments hereof also relate to a catheter for measuring a fractional flow reserve including a proximal shaft, a distal shaft coupled to the proximal shaft, a pressure sensor coupled to the distal shaft, at least one pressure sensor wire, and a movable shaft. The distal shaft is coupled to the proximal shaft. The distal shaft defines a guidewire lumen configured to receive a guidewire. The at least one pressure sensor wire is operably connected to the pressure sensor and extends proximally from the pressure sensor within the distal shaft proximally through the proximal shaft. The movable shaft includes a lumen sized to receive the proximal shaft. The catheter includes a first configuration with the movable shaft disposed over the proximal shaft and a second configuration with the movable shaft removed from the proximal shaft.

Embodiments hereof also related to a method for calculating a Fractional Flow Reserve in a vessel. The method includes delivering a catheter to a treatment site in the vessel. The catheter includes a pressure sensor coupled to a distal shaft, a proximal shaft, and a stiffening shaft disposed within an expansion lumen of the proximal shaft. The catheter is delivered to the treatment site with the stiffening shaft disposed in the expansion lumen and such that the pressure sensor is located on a distal side of a stenosis of the vessel. The method further includes removing the stiffening shaft from the expansion lumen such that the proximal shaft collapses from a radially expanded configuration to a radially collapsed configuration. The method further includes measuring a distal pressure distal of the stenosis using the pressure sensor and measuring a proximal pressure on a proximal side of the stenosis. The proximal pressure is measured with the proximal shaft in the radially collapsed configuration. The method further includes calculating the Fractional Flow Reserve using the measured distal pressure and the measured proximal pressure.

Embodiments hereof also relate to a method for calculating a Fractional Flow Reserve in a vessel. The method includes delivering a catheter to a treatment site in the vessel. The catheter includes a pressure sensor coupled to a distal shaft, a proximal shaft, and a movable shaft slidingly disposed around an outer surface of the proximal shaft. The catheter is delivered to the treatment site with the movable shaft disposed around the proximal shaft and such that the pressure sensor is located on a distal side of a stenosis of the vessel. The method further includes removing the movable shaft from around the proximal shaft. The method further includes measuring a distal pressure distal of the stenosis using the pressure sensor and measuring a proximal pressure on a proximal side of the stenosis. The proximal pressure is measured with the movable shaft removed from the proximal shaft. The method further includes calculating the Fractional Flow Reserve using the measured distal pressure and the measured proximal pressure.

Embodiments hereof also relate to a catheter for measuring a fractional flow reserve including a proximal shaft, a distal shaft coupled to the proximal shaft, a pressure sensor coupled to the distal shaft, and at least one pressure sensor wire operably connected to the pressure sensor. The proximal shaft includes a distal portion configured to extend through a stenosis in a vessel. The distal portion of the proximal shaft includes a radially expanded configuration having a first diameter and a radially collapsed configuration having a second diameter, wherein the first diameter is larger than the second diameter. The distal shaft includes a guidewire lumen configured to receive a guidewire therein. The at least one pressure sensor wire extends proximally from the pressure sensor through the distal shaft.

Embodiments hereof are also directed to a catheter for measuring a fractional flow reserve include a proximal shaft, a distal shaft coupled to the proximal shaft, a pressure sensor coupled to the distal shaft, and at least one pressure sensor wire operably connected to the pressure sensor. The distal shaft includes a distal portion and a collapsible portion proximal of the distal portion. The collapsible portion includes a radially expanded configuration having a first diameter and a radially collapsed configuration having a second diameter, wherein the first diameter is larger than the second diameter. A guidewire lumen extends through the collapsible portion and the distal portion of the distal shaft. The guidewire lumen is configured to receive a guidewire therein. The collapsible portion is in the radially expanded configuration with a guidewire disposed in the guidewire lumen of the collapsible portion, and the collapsible portion is in the radially collapsed configuration when the guidewire is removed from the guidewire lumen of the collapsible portion.

Embodiments hereof are also direct to method for calculating a Fractional Flow Reserve in a vessel. The method includes delivering a catheter to a treatment site in the vessel. The catheter includes a pressure sensor coupled to a distal portion of the catheter. The catheter is delivered to the treatment site such that the pressure sensor is located on a distal side of a stenosis of the vessel and a radially expandable portion of the catheter is disposed through the stenosis. The catheter is delivered to the treatment site with the radially expandable portion in a radially expanded configuration having a first diameter. The method further includes collapsing the radially expandable portion to a radially collapsed configuration having a second diameter smaller than the first diameter. The method further includes measuring a distal pressure distal of the stenosis using the pressure sensor. The distal pressure is measured with the radially expandable portion in the radially collapsed configuration. The method further includes measuring a proximal pressure proximal of the stenosis. The method further includes calculating the Fractional Flow Reserve using the measured distal pressure and the measured proximal pressure.

BRIEF DESCRIPTION OF DRAWINGS

FIG. 14A is a cross-sectional illustration of an embodiment of the distal portion of the proximal shaft of the catheter of FIG. 12, taken along line 134-14A of FIG. 12.

FIG. 14B is a cross-sectional illustration of an embodiment of the distal portion of the proximal shaft of the catheter of FIG. 13, taken along line 14B-14B of FIG. 13.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a vessel or a stenosis are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the following detailed description.

Figure 1:
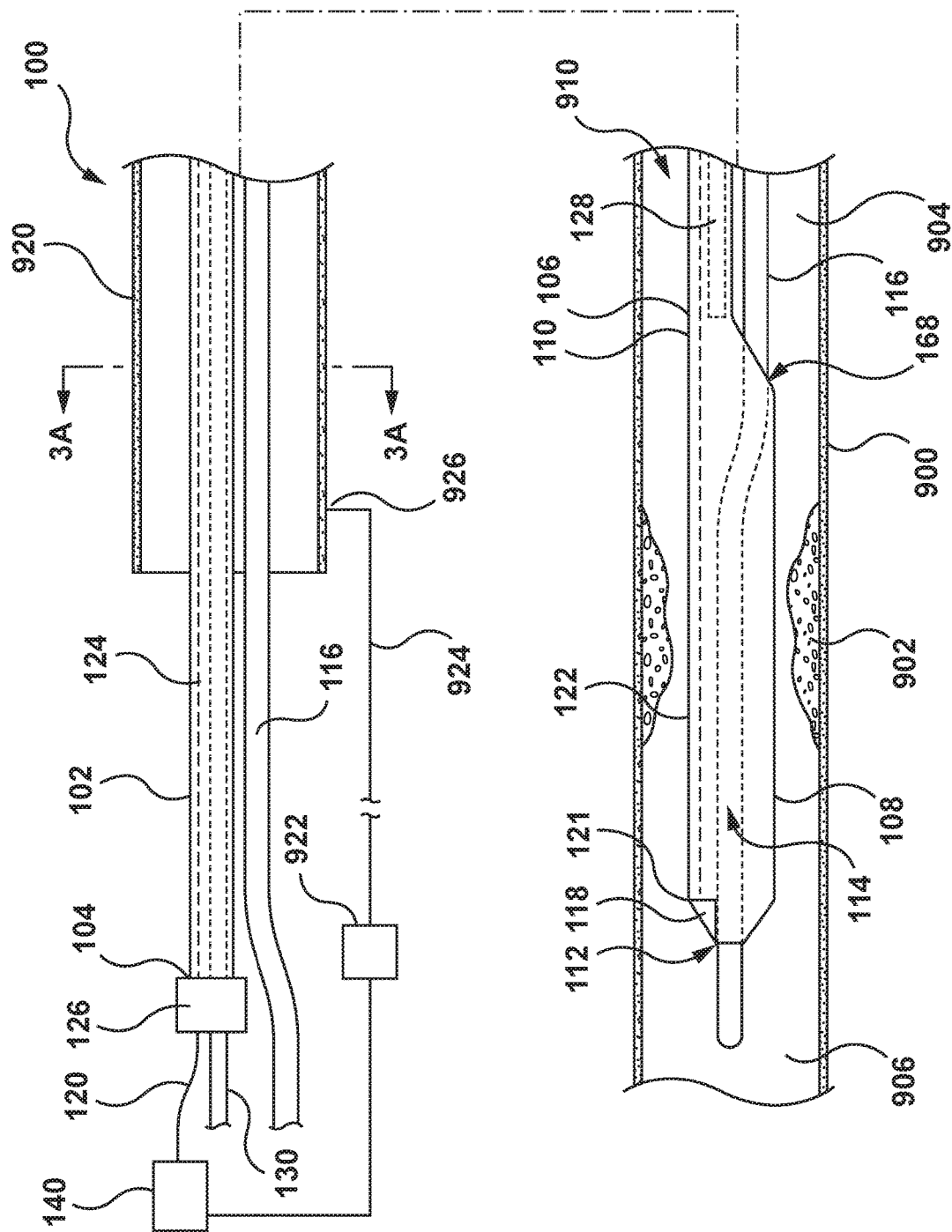
FIG. 1 is a side illustration of a catheter for calculating a Fractional Flow Reserve (FFR) in accordance with an embodiment hereof, with a proximal shaft in a radially expanded configuration.
Figure 2:
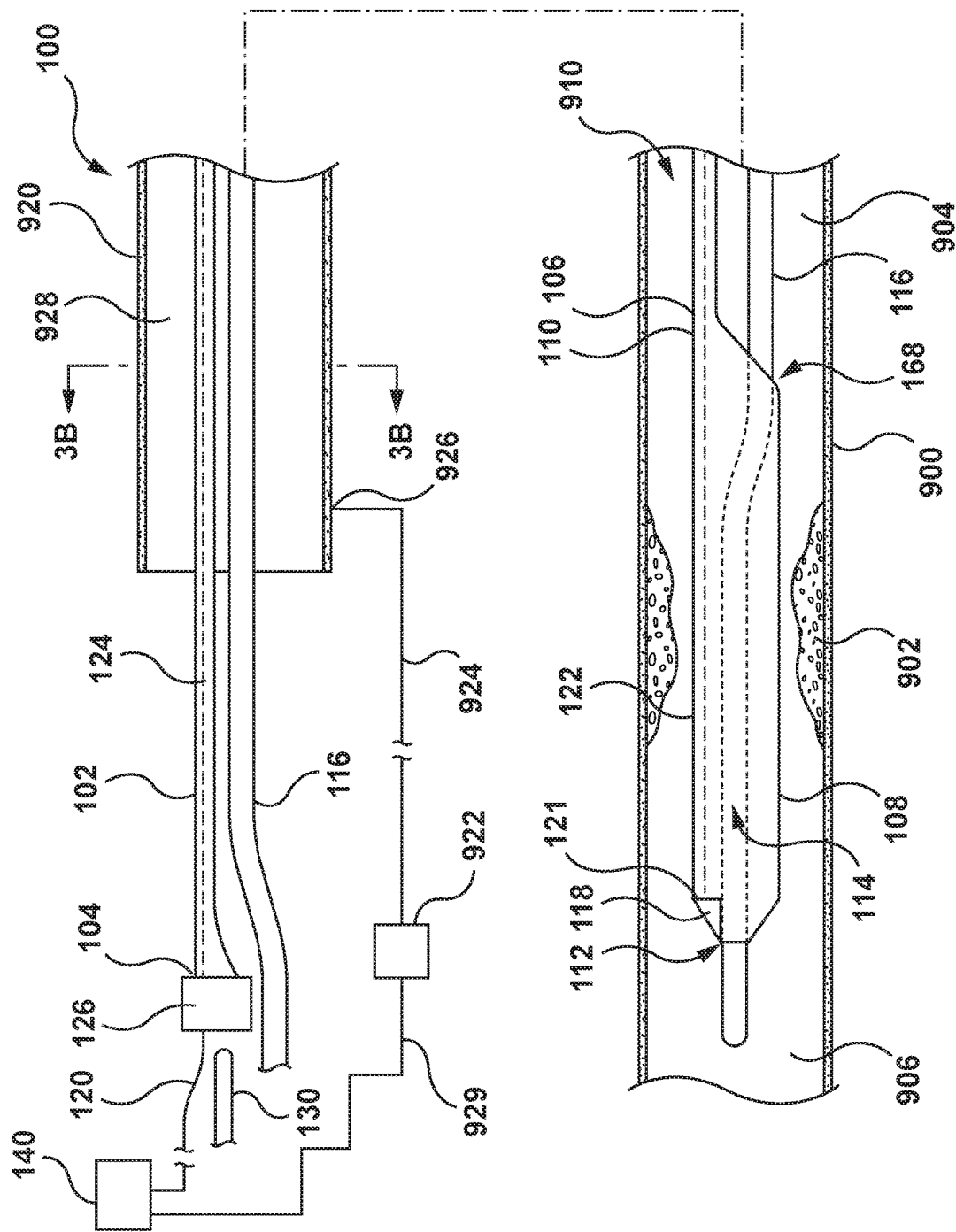
FIG. 2 is a side illustration of the catheter of FIG. 1 with the proximal shaft in a radially collapsed configuration.

Referring to FIGS. 1-4, a catheter (or micro-catheter) 100 for calculating a Fractional Flow Reserve (FFR) according to an embodiment of the present disclosure is shown. The catheter 100 includes a proximal shaft 102, a distal shaft 108, a pressure sensor 118, and at least one pressure sensor wire 120. The catheter 100 may further include a hub or handle 126 coupled to a proximal end of the proximal shaft 102 for convenient handling of the catheter 100, as shown in FIGS. 1 and 2. The catheter 100 is configured to be disposed in a vessel 900 with a proximal portion of the proximal shaft 102 extending outside of a patient, and a distal portion of the distal shaft 108 positioned in situ within a lumen 910 of the vessel 900 having a lesion or stenosis 902. The catheter 100 is configured to measure a distal pressure $P_d$ on a distal side 906 of the stenosis 902. Various features of the components of the catheter 100 reflected in FIGS. 1-4 and described below can be modified or replaced with different structures and/or mechanisms.

Figure 3A:
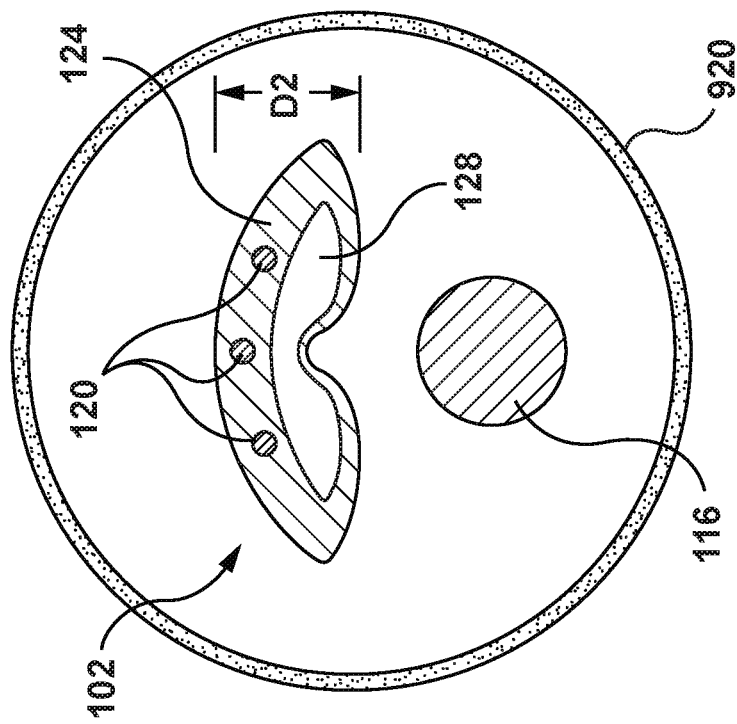
FIG. 3A is a cross-sectional illustration of an embodiment of the proximal shaft of the catheter of FIG. 1, taken along line 3A-3A of FIG. 1.
Figure 3B:
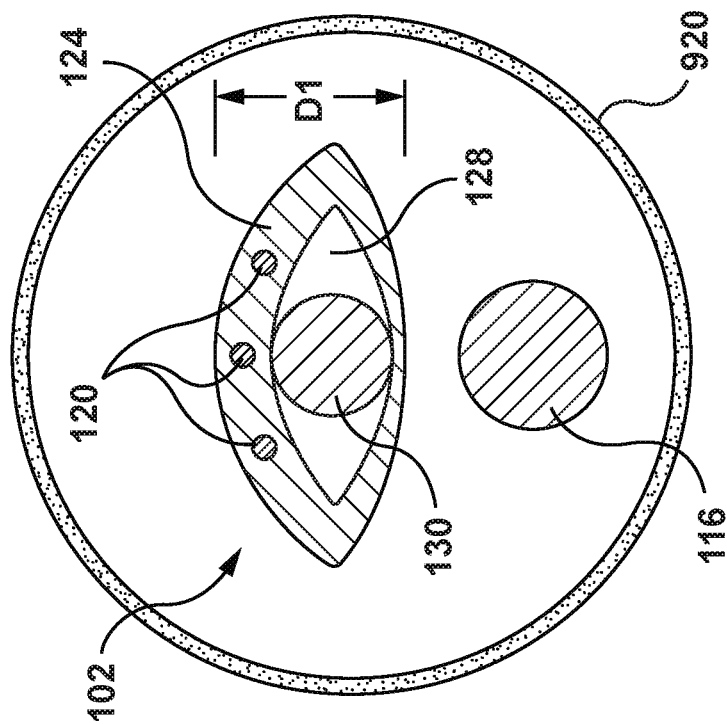
FIG. 3B is a cross-sectional illustration of an embodiment of the proximal shaft of the catheter of FIG. 2, taken along line 3B-3B of FIG. 2.

In an embodiment, the proximal shaft 102 of the catheter 100 includes a proximal end 104 and a distal end 106. The proximal shaft 102 includes an expansion lumen 128 extending therethrough from the proximal end 104 to the distal end 106, as shown in FIG. 1. However, it is not necessary for the expansion lumen 128 to extend to the distal end 106 of the proximal shaft. In other embodiments, the expansion lumen 128 may stop proximally of the distal end 106, but preferably at least to a location where the proximal shaft 102 exits the guide catheter 920 (described below). The proximal shaft 102 includes a radially expanded configuration (FIGS. 1 and 3A) and a radially collapsed configuration (FIGS. 2 and 3B). The expansion lumen 128 of the proximal shaft 102 is configured to receive a stiffening shaft 130 such that with the stiffening shaft 130 received with the expansion lumen 128, the proximal shaft 102 is in the radially expanded configuration and with the stiffening shaft 130 not received within the expansion lumen 128, the proximal shaft 102 is in the radially collapsed configuration. Thus, the proximal shaft 102 has a first outer diameter D1 when in the radially expanded configuration and a second outer diameter D2 when in the radially collapsed configuration, with the first outer diameter D1 being greater than the second outer diameter D2, as shown in FIGS. 3A-3B. As used herein, the term "diameter" does not have to refer to a circular profile, but instead is used generally to refer to a cross-sectional dimension.

The proximal shaft 102 may be formed of a shape-memory material with a pre-set shape. In the embodiment of FIGS. 1-3B, the proximal shaft 102 has a pre-set shape in the radially collapsed configuration, as shown in FIGS. 2 and 3B. Due to the shape memory material and pre-set shape thereof, the proximal shaft 102 actively recoils to the radially collapsed configuration upon removal of the stiffening shaft 130 from the expansion lumen 128. The proximal shaft 102 may be formed of, for example, and not by way of limitation, polyether block amide (e.g., VESTAMID or PEBAX), thermoplastic elastomers (TPE), or other materials suitable for the purposes described herein. The proximal shaft 102 may be coupled to the hub/handle 126 by, for example, and not by way of limitation, adhesives, mechanical connection, fusing, welding, for any other method suitable for the purposes of the present disclosure.

FIGS. 1-2 show an embodiment of the distal shaft 108 of the catheter 100. The distal shaft 108 includes a proximal end 110 and a distal end 112. A guidewire lumen 114 extends from the proximal end 110 to the distal end 112. The distal shaft 108 further includes the pressure sensor 118 and a distal portion of the pressure sensor wire 120. The distal shaft 108 is configured to extend from a proximal side 904 of the stenosis 902 to the distal side 906 of stenosis 902 such that the pressure sensor 118 is disposed on the distal side 906 of stenosis 902, as shown in FIGS. 1-2. The guidewire lumen 114 is configured to receive a guidewire 116 therein. A proximal guidewire port 168 is disposed at the proximal end 110 of the distal shaft 108. A distal guidewire port 113 is disposed at the distal end 112 of the distal shaft 108. The distal portion of the pressure sensor wire 120 is disposed within a distal shaft wall 122 of the distal shaft 108. The distal shaft 108 may be formed of, for example, and not by way of limitation, polyethylene, polyether block amide (e.g., VESTAMID or PEBAX), polyamide and/or combinations thereof, either blended or co-extruded, or other materials suitable for the purposes described herein. The distal shaft 108 may be coupled to the proximal shaft 102 by, for example, and not by way of limitation, adhesives, fusing, welding, for any other method suitable for the purposes of the present disclosure. In other embodiments, the proximal shaft 102 and the distal shaft 108 may be formed unitarily.

The pressure sensor 118 of the distal shaft 108, as shown in FIGS. 1-2, may be a piezo-resistive pressure sensor, a piezo-electric pressure sensor, a capacitive pressure sensor, an electromagnetic pressure sensor, an optical pressure sensor, and/or combinations thereof or other sensors suitable for the purpose described herein. The pressure sensor 118 is configured to measure a pressure of a fluid outside the distal shaft 108. With the pressure sensor 118 disposed on the distal side 906 of the lesion 902, the pressure sensor 118 measures the distal pressure $P_d$ of a fluid outside of the distal shaft 108. The pressure sensor 118 is further configured to communicate the distal pressure $P_d$ with a processor 140. The pressure sensor 118 is coupled to the distal shaft 108 of the catheter 100 such that the pressure sensor 118 is disposed on the distal side 906 of stenosis 902 when the distal shaft 108 is positioned at a treatment site therein, as shown in FIGS. 1-2. The pressure sensor 118 is coupled to the distal shaft 108 by, for example and not by way of limitation, adhesives, fusing, welding, for any other method suitable for the purposes of the present disclosure. Further, additional features may be provided as part of the distal shaft 108 for housing the pressure sensor 118, such as pockets, openings, and similar features.

The pressure sensor wire(s) 120 include(s) a proximal end coupled to the processor 140 and a distal end 121 coupled to the pressure sensor 118. The pressure sensor wire(s) 120 is/are configured such that pressure sensor 118 is in communication with the processor 140. The pressure sensor wire(s) 120 may be disposed within the proximal shaft wall 124 of the proximal shaft 102 and a corresponding distal shaft wall 122 of the distal shaft 108 such that the pressure sensor wire(s) 120 extend(s) proximally from the pressure sensor 118, through the distal shaft wall 122, through the corresponding proximal shaft wall 124, exiting through the hub/handle 126 to the processor 140. The pressure sensor wire(s) 120 may be coupled to the pressure sensor 118 by, for example, and not by way of limitation, adhesives, fusing, welding, or any other method suitable for the purposes of the present disclosure. The pressure sensor wire(s) 120 may be coupled to the processor 140 by, for example and not by way of limitation, cables, connectors, antennas, routers, switches, or any other coupling suitable for the purposes described herein.

While FIGS. 3A-3B show three (3) pressure sensor wires 120, this is not meant to limit the design, and more or fewer pressure sensor wires 120 may be utilized. Moreover, the pressure sensor wires 120 may be eliminated in embodiments wherein a signal from the pressure sensor 118 is sent to the processor 140 other than via the pressure sensor wires 120, such as, but not limited to, a wireless transmission.

The processor 140 may be any processor suitable for the purposes described herein. The processor 140 may include such components as a CPU, a display device, an amplification and filtering device, an analog-to-digital converter, and various other components. The processor 140 is configured to receive a measured proximal pressure $P_a$ and a measured distal pressure $P_d$. The processor 140 is further configured to provide a continuous display of calculated Fractional Flow Reserve (FFR). The processor 140 is coupled to the pressure sensor wires(s) 120 such that the processor 140 is in communication with the pressure sensor 118 as described previously. The processor 140 may be coupled to a proximal end of the pressure sensor wire(s) 120 via various communication pathways, including but not limited to one or more physical connections including electrical, optical, and/or fluid connections, a wireless connection, and/or combinations thereof. Accordingly, it is understood that additional components (e.g., cables, connectors, antennas, routers, switches, etc.) not illustrated in FIGS. 1-4 may include devices to facilitate communication between the proximal end of the pressure sensor wire(s) 120 and the processor 140. In other embodiments, instead of the pressure sensor wire(s) 120, communication between the pressure sensor 118 and the processor 140 may be accomplished wirelessly.

The stiffening shaft 130 may be a solid core wire. The stiffening shaft 130 is configured to be movable within the expansion lumen 128 of the proximal shaft 102, as shown in FIGS. 1-2. The stiffening shaft 130 is further configured such that when disposed within the expansion lumen 128 of the proximal shelf 102, the stiffening shaft 130 expands the proximal shaft 102 to the radially expanded configuration (FIGS. 1 and 3A). The stiffening shaft 130, when so disposed, is configured to provide strength and pushability to the proximal shaft 102 for delivery of the catheter 100 to the desired treatment site. The stiffening shaft 130 is further configured such that upon removal from the expansion lumen 128 of the proximal shaft 102, the proximal shaft 102 collapses to the radially collapsed configuration (FIGS. 2 and 3B). An outer surface of the stiffening shaft 130 may have a lubricious coating thereon. The stiffening shaft 130 may be formed of, for example, and not by way of limitation, metals such as stainless steel, cobalt, chromium, nickel and/or molybdenum based alloys (MP35N, MP20N, L605), nickel titanium alloys (NITINOL) or combinations thereof. The stiffening shaft 130 may be made of other materials provided that the stiffening shaft provides sufficient strength and pushability for the purposes described herein. The lubricious coating on the outer surface of the stiffening shaft 130 may be polytetrafluoroethylene (PTFE) or any other materials suitable for purposes of the present disclosure.

Figure 4:
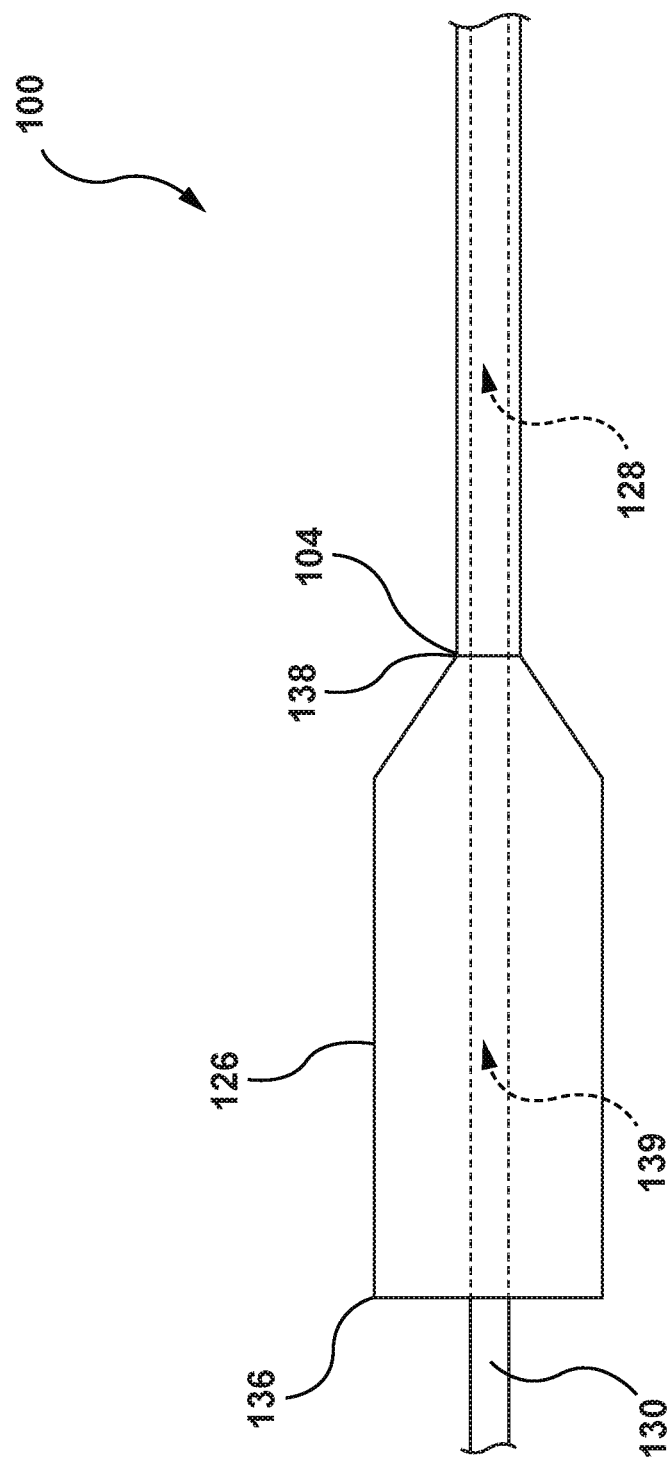
FIG. 4 is a side illustration of an embodiment of a stiffening shaft and hub of the catheter of FIG. 1.

In an embodiment shown in FIG. 4, the hub 126 of the catheter 100 includes a proximal end 136 and a distal end 138. The hub 126 defines a stiffening shaft lumen 139 therein between the proximal end 136 and the distal end 138. The stiffening shaft lumen 139 is disposed within the hub 126 such that the stiffening shaft lumen 139 aligns longitudinally with the expansion lumen 128, effectively creating a continuous lumen from proximal end 136 of the hub 126 extending distally through the proximal end 104 of the proximal shaft 102 to the distal end 106 of the proximal shaft 102 (FIG. 1) and configured to receive the stiffening shaft 130 therein. The stiffening shaft 130 is configured to be movable within both the stiffening shaft lumen 139 of hub 126 and the expansion lumen 128 of the proximal shaft 102.

With an understanding of the components of catheter 100, it is now possible to describe the interactions of the various components and a method to calculate a Fractional Flow Reserve (FFR). Referring back to FIGS. 1-2, a guide catheter 920 and the guidewire 116 are advanced through the vasculature to a desired site. The guidewire 116 may be back-loaded into the catheter 100 (i.e., the proximal end of the guidewire 116 is loaded into the distal end of the guidewire lumen 114 at the distal end 112 of distal shaft 108). The catheter 100, with the proximal shaft 102 in the radially expanded configuration (i.e., with the stiffening shaft 130 disposed within the expansion lumen 128) may then be advanced over the guidewire 116 and through a lumen 928 of the guide catheter 920 to the desired treatment site. In particular, with a distal end (not shown) of the guide catheter 920 disposed at a desired site proximal of the stenosis 902, such as in the sinus of an aortic valve, the distal shaft 108 of the catheter 100 is advanced through the lumen 928 and distal of the distal end of the guide catheter 920. The catheter 100 is advanced such that distal shaft 108 is disposed across the stenosis 902 of the vessel 900.

With the catheter 100 in position at the treatment site, the stiffening shaft 130 is removed from the expansion lumen 128 of the proximal shaft 102. Removing the stiffening shaft 130 results in the proximal shaft 102 collapsing to the radially collapsed configuration with second outer diameter D2, as shown in FIGS. 2 and 3B. With the proximal shaft 102 in the radially collapsed configuration, the combination of the guidewire 116 and the proximal shaft 102 occupies a smaller percentage of the lumen 928 of the guide catheter 920, as shown by comparing FIG. 3B to FIG. 3A. With the catheter 100 in position and the proximal shaft 102 in the radially collapsed configuration, the appropriate pressure measurements may be taken. Thus, blood flow adjacent the distal end of the guide catheter 920 fills the lumen 928 and tubing 924 via a port 926 in a proximal portion of the guide catheter 920. The proximal pressure $P_a$ at the distal end of the guide catheter 920 is measured by an external pressure transducer 922 via the fluid (blood) column extending through the lumen 928 and the tubing 922. Thus, the external pressure transducer 922 is configured to measure proximal or aortic (AO) pressure $P_a$ at the distal end of the guide catheter 920.

The external pressure transducer 922 is configured to communicate the measured proximal pressure $P_a$ to the processor 140 via a pressure transducer wire 929, as shown in FIG. 2. However, this is not meant to limit the design and the external pressure transducer 922 may communicate with the processor 140 by any means suitable for the purposes described, including, but not limited to, electrical cables, optical cables, or wireless devices. Simultaneously, the pressure sensor 118 measures distal pressure $P_d$ distal of the stenosis 902. The distal pressure $P_d$ is communicated to the processor 140, as explained above. The processor 140 calculates the Fractional Flow Reserve (FFR) based on the distal pressure $P_d$ divided by the proximal/aortic pressure $P_a$, or $FFR = P_d/P_a$.

As explained above, the catheter 100 with the proximal shaft 102 in the radially collapsed configuration has a reduced cross-sectional profile (FIG. 3B) as compared to the proximal shaft 102 in the radially expanded configuration (FIG. 3A). As further explained above, because the proximal or aortic pressure $P_a$ is measured using the fluid column within the lumen 928 of the guide catheter 920 between an outer surface of a guidewire/proximal shaft combination and an inner surface of the guide catheter, a larger profile may lead to errors in the measured proximal or aortic pressure $P_a$. Such errors are carried through to the FFR calculation noted above because the measured proximal pressure $P_a$ is used in the FFR calculation. Thus, reducing the cross-sectional profile leads to a smaller potential for error in the proximal pressure $P_a$, and hence a smaller potential for error in the FFR calculation. Since the size of the guidewire 116 remains constant, the smaller the cross-sectional profile of the proximal shaft 102, the smaller the potential error in proximal (AO) pressure measurement $P_a$. Stated another way, the smaller the cross-sectional profile of the proximal shaft 102 of the catheter 100, the more accurate the proximal (AO) pressure measurement $P_a$, and therefore a more accurate FFR value.

Referring to FIGS. 5-8B, a catheter (or micro-catheter) 200 for calculating a Fractional Flow Reserve (FFR) according to another embodiment of the present disclosure is shown. The catheter 200 includes a proximal shaft 202, a distal shaft 208, a pressure sensor 218, and at least one pressure sensor wire 220, as shown in FIGS. 5-7B and described in greater detail below. The distal shaft 208, the pressure sensor 218, and the at least one pressure sensor wire 220 are similar to the distal shaft 108, the pressure sensor 118, and the at least one pressure sensor wire 120 of the catheter 100 of FIGS. 1-4. Therefore, details of the distal shaft 208, the pressure sensor 218, and the at least one pressure sensor wire 220 will not be repeated here. The catheter 200 is configured to be disposed with a proximal portion of the proximal shaft 202 extending outside of a patient, and a distal portion of the distal shaft 208 positioned in situ within a lumen 910 of a vessel 900 having a stenosis or lesion 902. The catheter 200 is configured such that the catheter 200 measures a distal pressure $P_d$ of blood on a distal side 906 of the stenosis 902.

Figure 5:
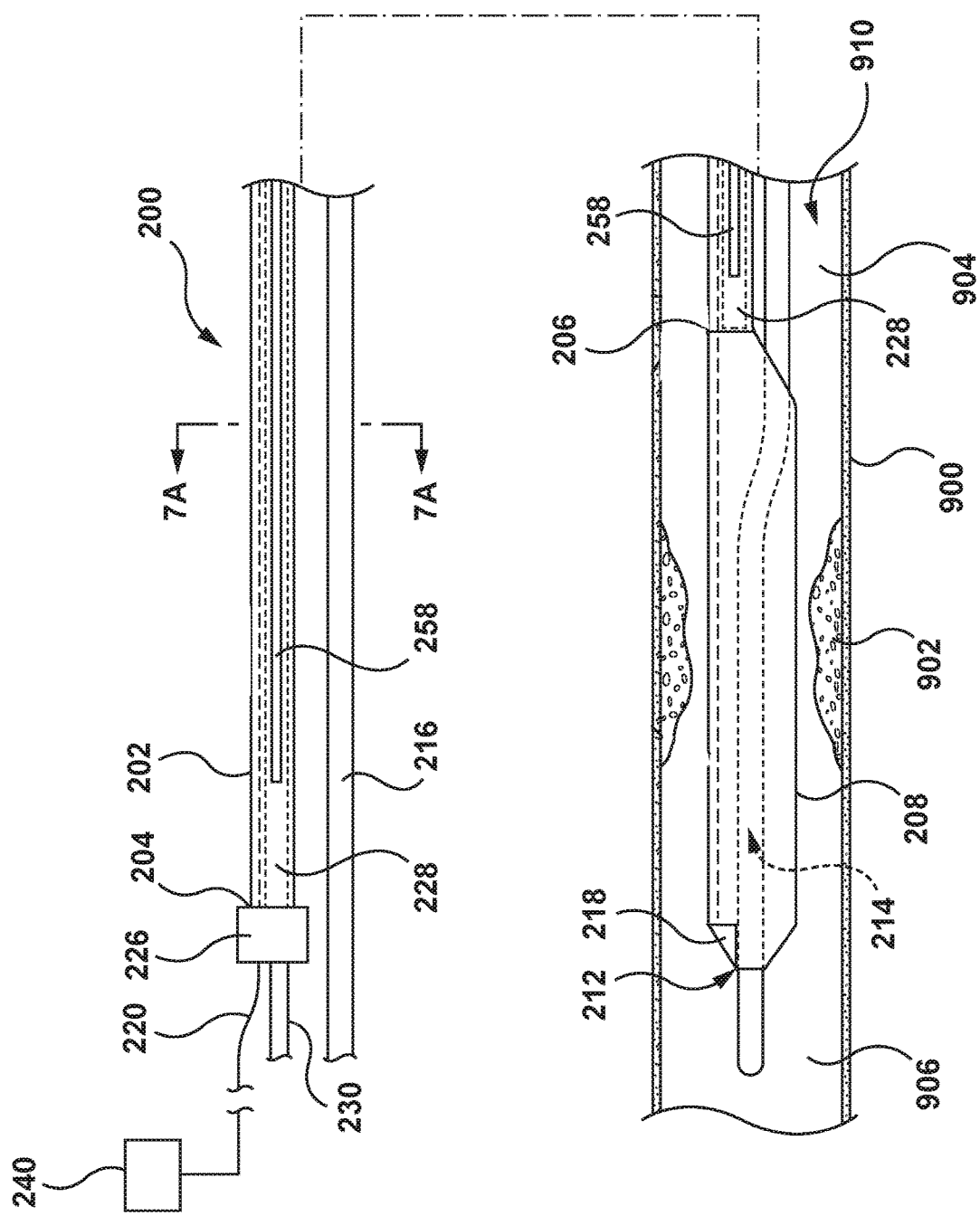
FIG. 5 is a side illustration of another embodiment of a catheter for calculating a Fractional Flow Reserve (FFR) with the proximal shaft in the radially expanded configuration.
Figure 6:
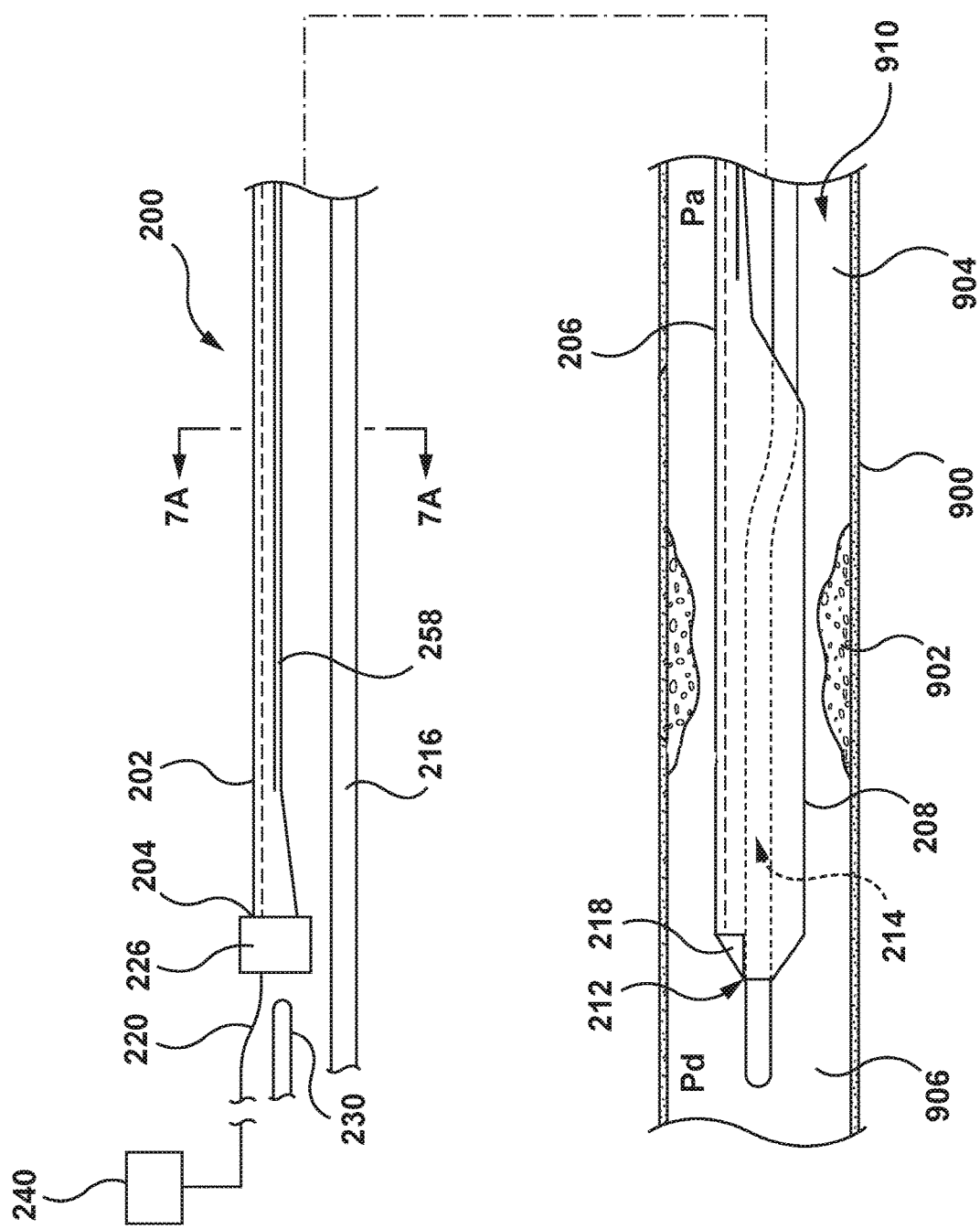
FIG. 6 is a side illustration of the catheter of FIG. 5 with the proximal shaft in the radially collapsed configuration.
Figures 7A, 7B:
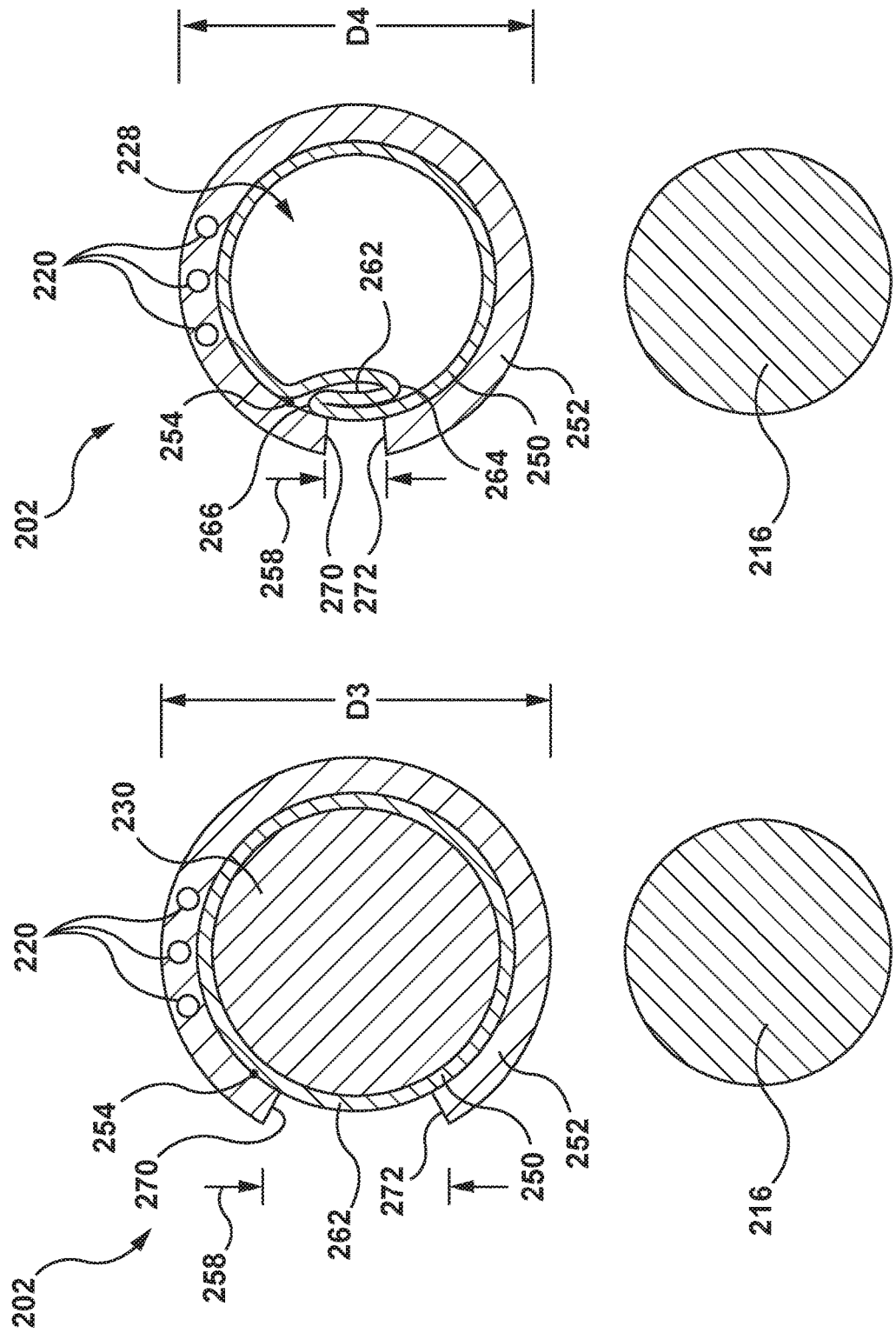
FIG. 7A is a cross-sectional illustration of an embodiment of the proximal shaft of the catheter of FIG. 5, taken along line 7A-7A of FIG. 5.
FIG. 7B is a cross-sectional illustration of an embodiment of the proximal shaft of the catheter of FIG. 6, taken along line 7B-7B of FIG. 6.

In an embodiment, the proximal shaft 202 of the catheter 200 includes a proximal end 204, a distal end 206, and an expansion lumen 228 extending from the proximal end 204 to the distal end 206 of the proximal shaft 202. However, it is not necessary for the expansion lumen 228 to extend to the distal end 206 of the proximal shaft 202. In other embodiments, the expansion lumen 228 may stop proximally of the distal end 206, but preferably extends distally at least to a location where the proximal shaft 202 exits the guide catheter. The proximal shaft 202 includes a radially expanded configuration (FIGS. 5 and 7A) and a radially collapsed configuration (FIGS. 6 and 7B). The expansion lumen 228 of the proximal shaft 202 is configured to receive a stiffening shaft 230 such that with the stiffening shaft 230 received within expansion lumen 228, the proximal shaft 202 is in the radially expanded configuration, and with the stiffening shaft 230 not received with expansion lumen 228, the proximal shaft 202 is in the radially collapsed configuration. The proximal shaft 202 has a first outer diameter D3 when in the radially expanded configuration and a second outer diameter D4 when in the radially collapsed configuration, with the first outer diameter D3 being greater than the second outer diameter D4, as shown in FIGS. 7A-7B. The proximal shaft 202 is disposed distal of and coupled to a hub 226 for convenient handling of the catheter 200. The proximal shaft 202 may be coupled to the hub 226 by, for example and not by way of limitation, adhesives, fusing, welding, for any other method suitable for the purposes of the present disclosure.

The proximal shaft 202 may be formed of a shape-memory configuration with a pre-set shape, non-limiting examples of which are described in U.S. Pat. No. 9,192,751 to Macaulay et al., which is incorporated by reference herein in its entirety. In the embodiment of FIGS. 5-7B, the proximal shaft 202 has a pre-set shape in the radially collapsed configuration with the second outer diameter D4. Due to the shape memory material and pre-set shape thereof, the proximal shaft 202 of the catheter 200 actively recoils to the radially collapsed configuration after removal of the stiffening shaft 230 from the expansion lumen 228.

FIGS. 7A-7B illustrate an embodiment of how the proximal shaft 202 is configured to collapse upon removal of the stiffening shaft 230 from the expansion lumen 228. In such an embodiment, the proximal shaft 202 includes an elastic frame 254, a liner 250, and a jacket 252. The elastic frame 254 may be coupled between the liner 250 and the jacket 252 by lamination, embedding, or other methods suitable for the purposes described herein. Although not shown in the drawings, elastic frame 254 is generally tubular. The elastic frame 254 may assume various shapes suitable for the purposes described herein, embodiments of which are described in detail in U.S. Pat. No. 9,192,751 to Macaulay et al., which is incorporated herein by reference in its entirety. Therefore, the details of elastic frame 254 will not be repeated here. The elastic frame 254 may be formed of materials such as, but not limited to, nickel-titanium alloys (e.g. NITINOL), nickel-cobalt-chromium-molybdenum alloys (e.g. MP35N), stainless steel, high spring temper steel, or any other metal or elastomer or composite having elastic properties to permit expansion and recoil suitable for purposes of the present disclosure. The liner 250 may be constructed of materials such as, but not limited to, polytetrafluoroethylene (PTFE; e.g. Teflon®), polyethylene, polyethylene terephthalate (PET), polyester, or other materials suitable for the purposes of the present disclosure. The jacket 252 may be constructed of materials such as, but not limited to, polyurethane (e.g. Peliethane©, Eiasthane™, Texin®, Tecothane®), polyamide polyether block copolymer (e.g. Pebax®, nylon 12), polyethylene, TPE, Propel, Fuoroguard or other materials suitable for the purposes of the present disclosure.

The elastic frame 254 is of a shape memory material with a pre-set shape. In an embodiment, the elastic frame 254 has a pre-set shape in the radially collapsed configuration as shown in FIG. 7B. The elastic frame 254 enables the proximal shaft 202 to expand to the radially expanded configuration with the first outer diameter D3, as shown in FIG. 7A. Due to the shape memory material and pre-set shape thereof, the elastic frame 254 causes the proximal shaft 202 to actively recoil to the radially collapsed configuration after removal of the stiffening shaft 230 from the expansion lumen 228 of the proximal shaft 202.

The liner 250 is circumferentially continuous and forms the expansion lumen 228, as shown in FIG. 7A. The elastic frame 254 and the jacket 252 are non-circumferentially continuous. Accordingly, a circumferential jacket gap 258 is disposed between a first circumferential end 270 and a second circumferential end 272 of jacket 252, as shown in FIG. 7A. In the radially collapsed configuration, as shown in FIG. 7B, the liner 250 folds to form a liner overlap portion 262 defined by at least one fold. In one embodiment, overlap portion is defined by an inner fold 264 and an outer fold 266 of the liner 250. When the liner 250 folds by the radially collapse of the elastic frame 254, the liner 250 forms the liner overlap portion 262, and the first circumferential end 270 and the second circumferential 272 of the jacket 252 move closer together, as shown in FIG. 7B. Thus, the circumferential jacket gap 258 is reduced in size, as shown by comparing FIGS. 7A and 7B. In the radially expanded configuration, the inner fold 264 and the outer fold 266 are flattened or stretched apart such that the first and second circumferential ends 270, 272 of the jacket 252 move apart from each other, thereby increasing the circumferential jacket gap 258, as shown in FIG. 7A.

The stiffening shaft 230 may be a solid core wire, as explained above with respect to the stiffening shaft 130. The stiffening shaft 230 is configured to be movable within the expansion lumen 228 of the proximal shaft 202 as shown in FIGS. 5-6. The stiffening shaft 230 is further configured such that when disposed within the expansion lumen 228 of the proximal shaft 202, the stiffening shaft 230 expands the proximal shaft 202 to the radially expanded configuration (FIGS. 5 and 7A). The stiffening shaft 230, when so disposed, is configured to provide strength and pushability to the proximal shaft 202 for delivery of the catheter 200 to the desired treatment site. The stiffening shaft 230 is further configured such that upon removal of the stiffening shaft 230 from the expansion lumen 228 of the proximal shaft 202, the proximal shaft 202 collapses to the radially collapsed configuration (FIGS. 6 and 7B). An outer surface of the stiffening shaft 230 may have a lubricious coating thereon. The stiffening shaft 230 may be formed of, for example, and not by way of limitation, metals such as stainless steel, cobalt, chromium, nickel and/or molybdenum based alloys (MP35N, MP20N, L605), nickel titanium alloys (NITINOL) or combinations thereof. The stiffening shaft 230 may be made of other materials provided that the stiffening shaft provides sufficient strength and pushability for the purposes described herein. The lubricious coating on the outer surface of the stiffening shaft 230 may be polytetrafluoroethylene (PTFE) or any other materials suitable for purposes of the present disclosure.

Figure 8:
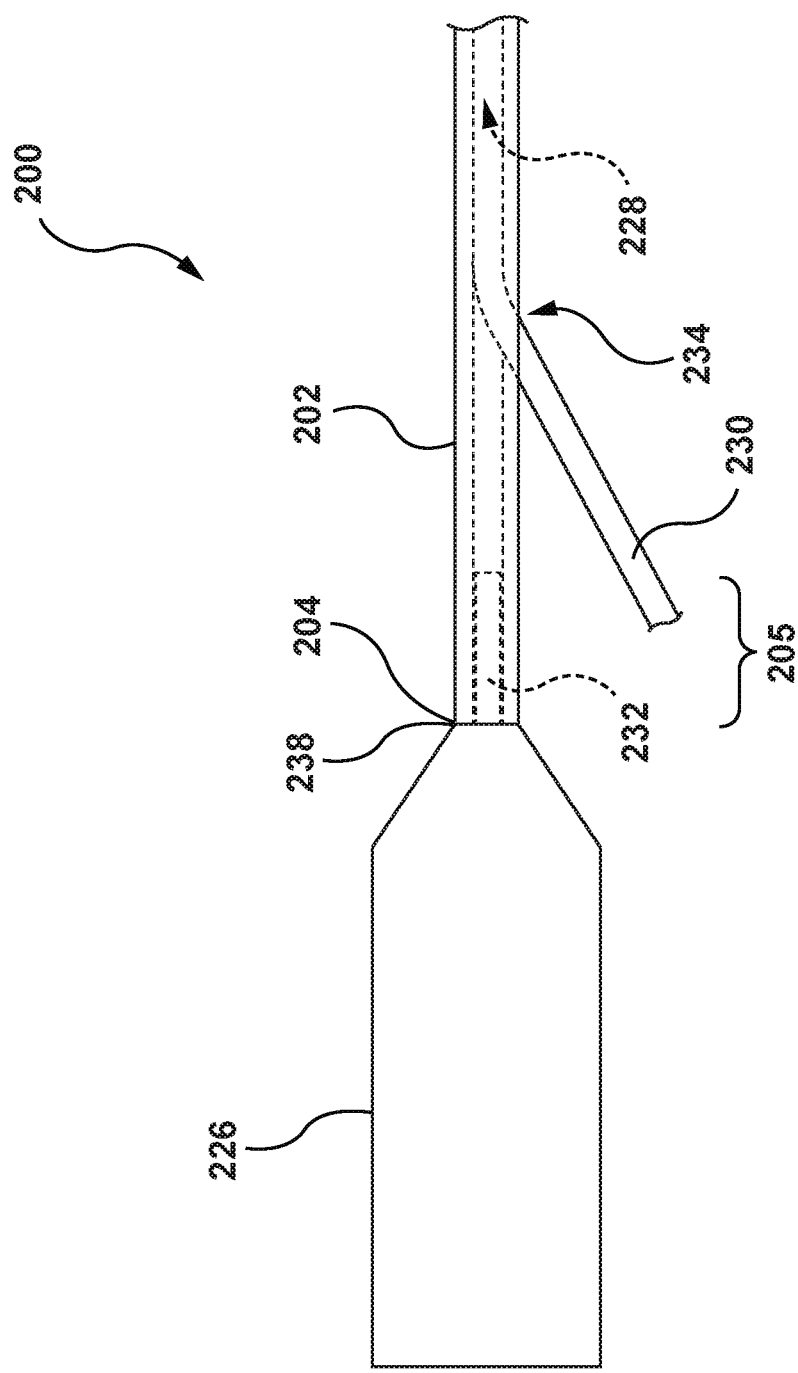
FIG. 8 is a side illustration of an embodiment of the stiffening shaft and hub of the catheter of FIG. 5.

In an embodiment shown in FIG. 8, the hub 226 of the catheter 200 includes a proximal end 236 and a distal end 238. A short stiff shaft 232 is coupled to the distal end 238 of the hub 226. The short stiff shaft 232 extends distally within a proximal portion 205 of the expansion lumen 228 of the proximal shaft 202. The short stiff shaft 232 provides strength and pushability to the proximal portion 205 of the proximal shaft 202. A stiffening shaft exit port 234 is in communication with the expansion lumen 228 for entry and exit of the stiffening shaft 230 to the expansion lumen 228.

The stiffening shaft 230 is configured to be movable within expansion shaft 228 via the stiffening shaft exit port 234. The design of the proximal shaft 202 with the stiffening shaft exit port 234 and the short stiff shaft 232 may be interchanged with other embodiments herein. For example, and not by way of limitation, the proximal shaft 102 of the embodiment of FIGS. 1-4 may be used with the stiffening shaft exit port 234 and the short stiff shaft 232 of the embodiment of FIGS. 5-8. Similarly, the proximal shaft 202 of the embodiment of FIGS. 5-8 may be used with the manner in which the stiffening shaft 130 is introduced and removed from the proximal shaft 102 of FIGS. 1-4.

With an understanding of the components of catheter 200, the interactions of the various components and a method to calculate a Fractional Flow Reserve (FFR) will now be described. Referring back to FIGS. 5-6, a guide catheter (not shown but may be similar to guide catheter 920 of FIGS. 1-2) and the guidewire 216 are advanced through the vasculature to a desired site. The guidewire 216 may be back-loaded into the catheter 200 (i.e., the proximal end of the guidewire 216 is loaded into the distal end of the guidewire lumen 214 at the distal end 212 of the distal shaft 208). The catheter 200, with the proximal shaft 202 in the radially expanded configuration (i.e., with the stiffening shaft 230 disposed within the expansion lumen 228) may then be advanced over the guidewire 216 and through a lumen of the guide catheter to the desired treatment site. In particular, with a distal end (not shown) of the guide catheter disposed at a desired site proximal of the stenosis 902, such as in the sinus of an aortic valve, the distal shaft 208 of the catheter 200 is advanced through the lumen of the guide catheter and distal of the distal end of the guide catheter. The catheter 200 is advanced such that distal shaft 208 is disposed through the stenosis 902 of the vessel 900.

With the catheter 200 in position at the treatment site, the stiffening shaft 230 is removed from the expansion lumen 228 of the proximal shaft 202. Removing the stiffening shaft 230 results in the proximal shaft 202 collapsing to the radially collapsed configuration with the second outer diameter D3, as shown in FIGS. 6 and 7B. With the proximal shaft 202 in the radially collapsed configuration, the combination of the guidewire 216 and the proximal shaft 202 occupies a smaller percentage of the lumen of the guide catheter, as shown by comparing FIG. 7B to FIG. 7A. With the catheter 200 in position and the proximal shaft 202 in the radially collapsed configuration, the appropriate pressure measurements may be taken. Thus, blood flow adjacent the distal end of the guide catheter fills the lumen of the guide catheter and tubing via a port in a proximal portion of the guide catheter. The proximal pressure $P_a$ at the distal end of the guide catheter is measured by an external pressure transducer via the fluid (blood) column extending through the lumen of the guide catheter and the tubing. Thus, the external pressure transducer is configured to measure the proximal or aortic (AO) pressure $P_a$ at the distal end of the guide catheter.

The external pressure transducer is configured to communicate the measured proximal pressure $P_a$ to a processor 240 via a pressure transducer wire, similar to as described above with respect to FIG. 2. Simultaneously, the pressure sensor 218 measures the distal pressure $P_d$ distal of the stenosis 902. The distal pressure $P_d$ is communicated to the processor 240, as explained above. The processor 240 calculates the Fractional Flow Reserve (FFR) based on the distal pressure $P_d$ divided by the proximal/aortic pressure $P_a$, or $FFR=P_d/P_a$.

As explained above, the catheter 200 with the proximal shaft 202 in the radially collapsed configuration has a reduced cross-sectional profile (FIG. 7B) as compared to the proximal shaft 202 in the radially expanded configuration (FIG. 7A). As further explained above, because the proximal or aortic pressure $P_a$ is measured using the fluid column within the lumen of the guide catheter between an outer surface of a guidewire/proximal shaft combination and an inner surface of the guide catheter, a larger profile may lead to errors in the measured proximal or aortic pressure $P_a$. Such errors are carried through to the FFR calculation noted above because the measured proximal pressure $P_a$ is used in the FFR calculation. Thus, reducing the cross-sectional profile leads to a smaller potential for error in the proximal pressure $P_a$, and hence a smaller potential for error in the FFR calculation. Since the size of the guidewire 216 remains constant, the smaller the cross-sectional profile of the proximal shaft 202, the smaller the potential error in measured proximal (AO) pressure $P_a$. Stated another way, the smaller the cross-sectional profile of the proximal shaft 202 of the catheter 200, the more accurate the measured proximal (AO) pressure $P_a$, and therefore a more accurate FFR value is calculated.

Referring to FIGS. 9-11B, a catheter (or micro-catheter) 500 for calculating a Fractional Flow Reserve (FFR) according to another embodiment of the present disclosure is shown. The catheter 500 includes a proximal shaft 502, a distal shaft 508, transition shaft 570, a pressure sensor 518, at least one pressure sensor wire 520, and a movable shaft 542. The distal shaft 508, the pressure sensor 518, and the at least one pressure sensor wire 520 are similar to the distal shaft 108, the pressure sensor 118, and the at least one pressure sensor wire 120 of the catheter 100 of FIGS. 1-4. Therefore, details of the distal shaft 508, the pressure sensor 518, and the at least one pressure sensor wire 520 will not be repeated here. The catheter 500 is configured to be disposed with a proximal portion of the proximal shaft 502 extending outside of a patient, and a distal portion of the distal shaft 508 positioned in situ within a lumen 910 of a vessel 900 having a stenosis or lesion 902. The catheter 500 is configured such that the catheter 500 measures a distal pressure $P_d$ of blood in the vessel 900 on a distal side 906 of the stenosis 902.

The catheter 500 includes a first configuration (FIGS. 9, 9A and 11A) with the movable shaft 542 disposed over the proximal shaft 502, and a second configuration (FIGS. 10, 10B and 11B) with the movable shaft 542 not disposed over the proximal shaft 502. The first configuration is generally used to deliver the catheter 500 through the vasculature to the desired treatment site. Thus, with the movable shaft 542 disposed over the proximal shaft 502, the movable shaft 542 provides strength and pushability to the proximal shaft 502. When at the desired treatment site, the movable shaft 542 may be retracted proximally such that the proximal shaft 502 occupies a smaller area of the guide catheter.

As noted above, the catheter 500 includes a transition shaft 570. The transition shaft 570 is disposed between the proximal shaft 502 and the distal shaft 508. Thus, a proximal end 572 of the transition shaft 570 is disposed adjacent a distal end 506 of the proximal shaft 502 and a distal end 574 of the transition shaft 570 is disposed adjacent a proximal end 510 of the distal shaft 508. The transition shaft 570 serves as a transition from the proximal shaft 502 to the distal shaft 508. The transition shaft 570 includes a guidewire port 576 for entry of the guidewire 516 into the transition shaft 570 and the distal shaft 508. Although the transition shaft 570 is described separately in the embodiment of FIGS. 9-11B, the transition shaft may be considered part of the distal shaft 508. Further, other embodiments described herein may include such a transition shaft even if not specifically described, and the present embodiment need not include a transition shaft.

In an embodiment, the proximal shaft 502 may be a hollow shaft with the pressure sensor wire(s) 520 disposed within a central passageway of the hollow shaft. The proximal shaft 502 includes a proximal end 504 coupled to a hub/handle 526 and a distal end 506 coupled to the transition shaft 570. The proximal shaft 502 is disposed distal of and coupled to a hub/handle 526. It is desirable for the proximal shaft to have a minimized cross-sectional profile in order to occupy a smaller percentage of a passageway of a guide catheter. In an embodiment, the proximal shaft 502 has an outer diameter of approximately 0.014 inch, which is equivalent to the outer diameter of FFR wires. The proximal shaft 502 may be formed of materials such as, but not limited to, stainless steel, cobalt, chromium, nickel and/or molybdenum based alloys (MP35N, MP20N, L605), nickel titanium alloys (NITINOL) or combinations thereof. The proximal shaft 502 may also be formed of materials such, but not limited to, polyethylene, polyether block amide (PEBA, e.g. VESTAMID, PEBAX), thermoplastic elastomers (TPE), polyamide and/or combinations thereof, either blended or co-extruded, or other materials suitable for the purposes described herein. The proximal shaft 502 may be coupled to the hub 526 by, for example, and not by way of limitation, adhesives, fusing, welding, for any other method suitable for the purposes of the present disclosure.

Figure 9:
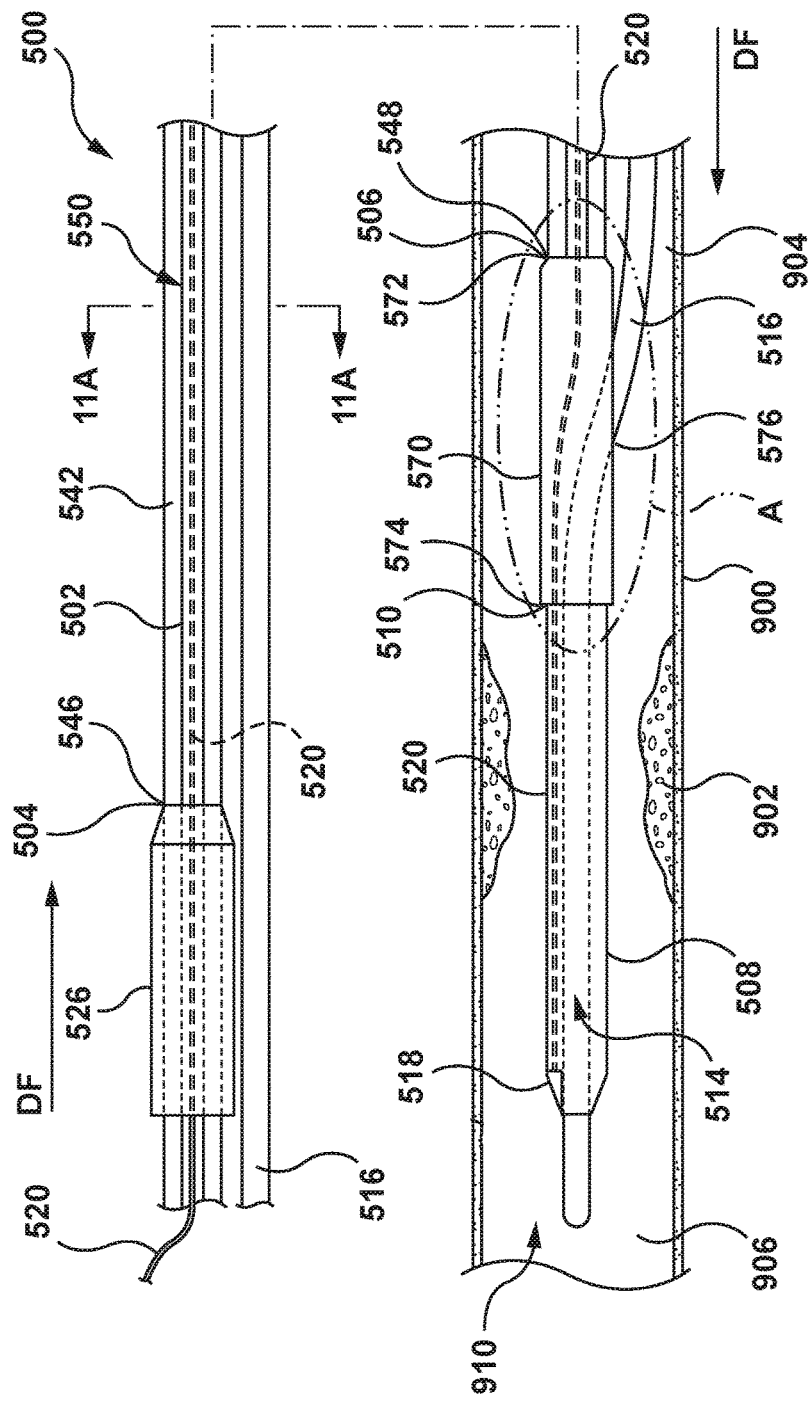
FIG. 9 is a side illustration of another embodiment of a catheter for calculating a Fractional Flow Reserve (FFR) in a first configuration.
Figure 9A:
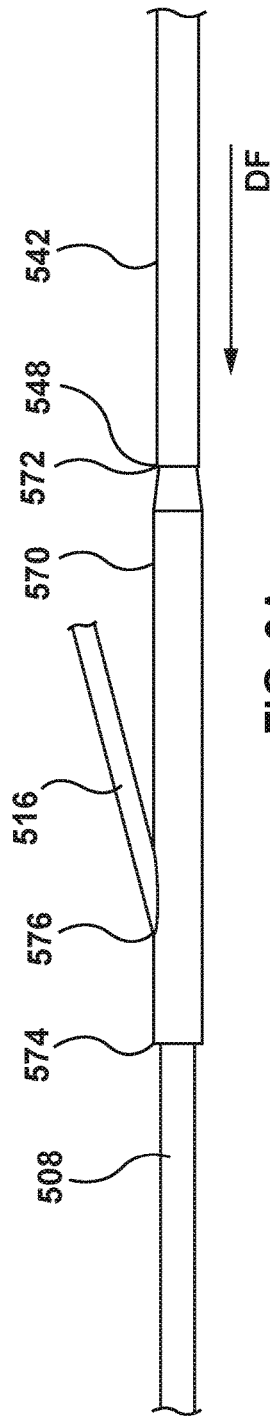
FIG. 9A is a detail view of portion A of FIG. 9.
Figure 10:
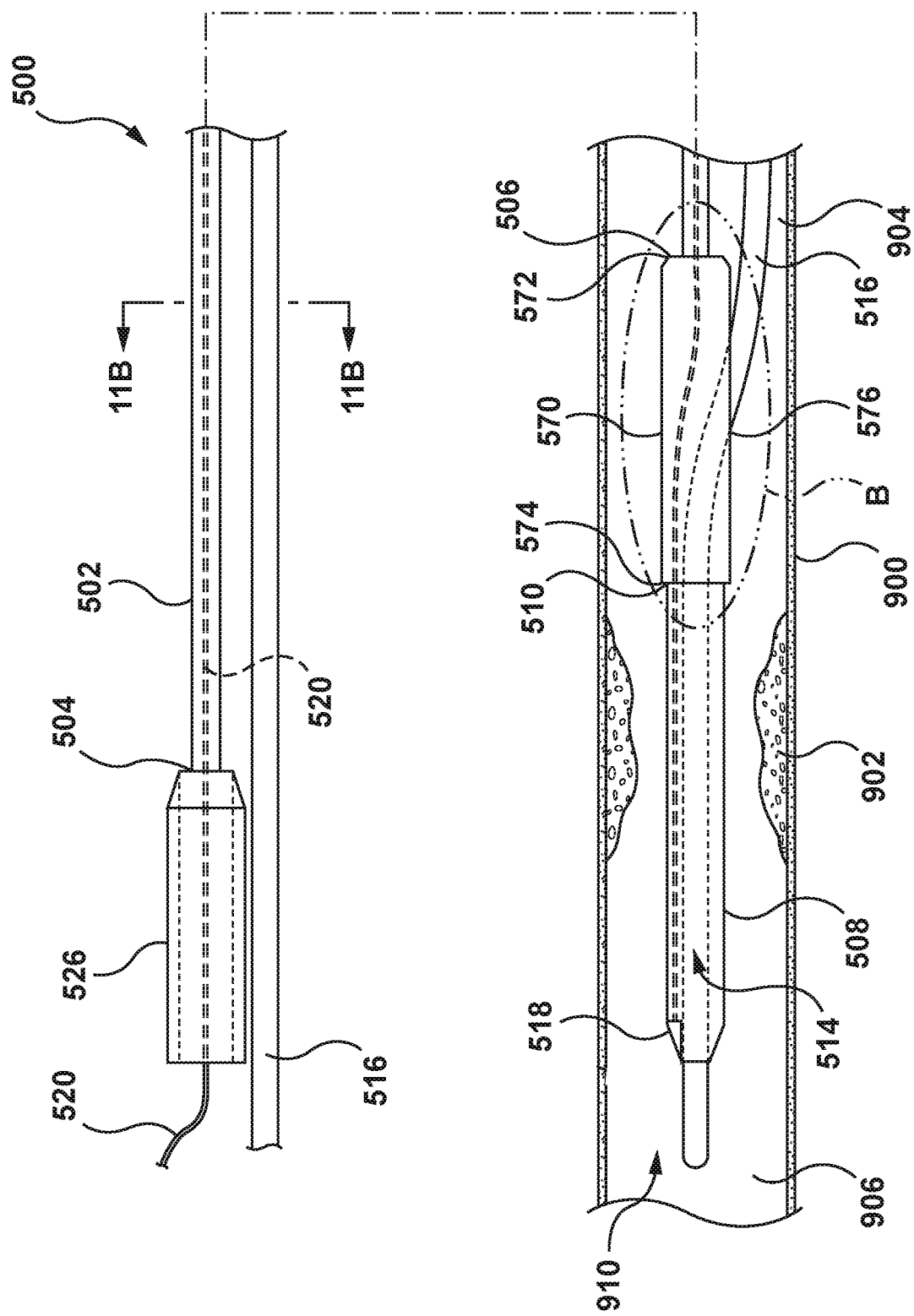
FIG. 10 is a side illustration of the catheter of FIG. 9 in a second configuration.
Figure 10A:
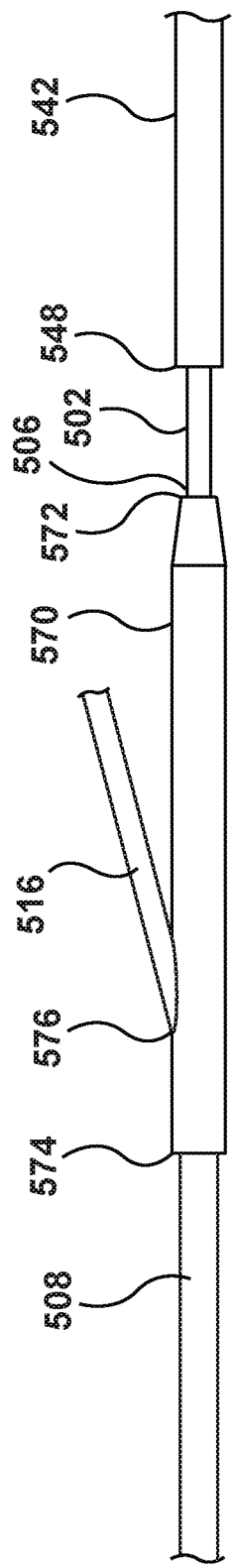
FIG. 10A is detailed view of section B of FIG. 10 as the movable shaft is being removed.
Figure 10B:
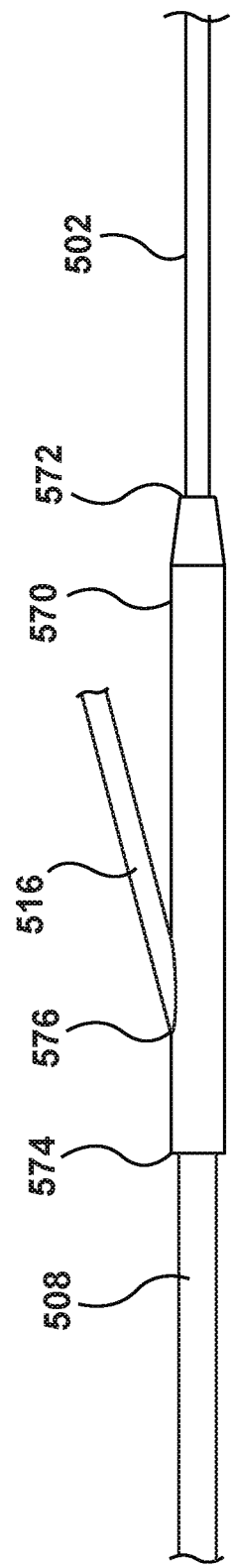
FIG. 10B is a detailed view of section B of FIG. 10 with the movable shaft removed.
Figure 11B:
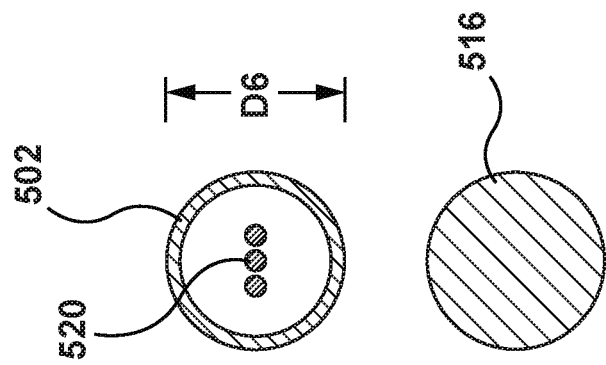
FIG. 11B is a cross-sectional illustration of an embodiment of the proximal shaft of the catheter of FIG. 10, taken along line 11B-11B of FIG. 10.
Figure 11A:
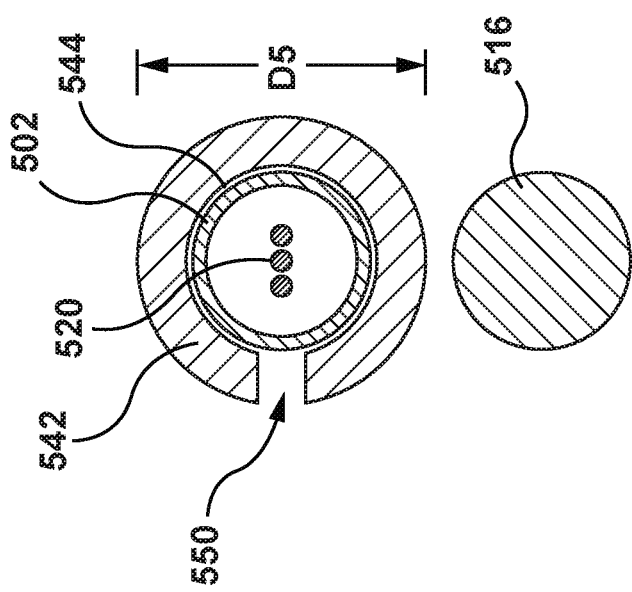
FIG. 11A is a cross-sectional illustration of an embodiment of a proximal shaft of the catheter of FIG. 9, taken along line 11A-11A of FIG. 9.

In an embodiment, the movable shaft 542 is generally tubular with a c-shape cross-section, as shown in FIGS. 9 and 11A. The movable shaft 542 includes a proximal end 546 and a distal end 548. The movable shaft 542 includes a lumen 544 extending from the proximal end 546 to the distal end 548 (FIG. 11A). The movable shaft 542 further includes a groove 550 extending longitudinally from the proximal end 546 distally to the distal end 548. The groove 550 also extends radially from an inner surface of the movable shaft 542 to an outer surface of the movable shaft 542, as shown in FIG. 11A. The movable shaft 542 is configured to be slidably disposed over the proximal shaft 502 such that when the movable shaft 542 is disposed over the proximal shaft 502, the catheter 500 is in the first configuration (FIGS. 9 and 11A), and when the movable shaft 542 is not disposed over the proximal shaft, the catheter 500 is in the second configuration (FIGS. 10 and 11B). The movable shaft 542 is further configured to be selectively coupled to the hub 526 such that with the movable shaft 542 disposed over the proximal shaft 502 and selectively coupled to the hub 526, the distal end 548 of the movable shaft 542 contacts a proximal end 572 of the transition shaft 570 (FIGS. 9, 9A) (the first configuration). In this first configuration, a distally directed force DF applied to the hub 526 is transferred to the movable shaft 542 coupled thereto. The distally directed force DF is transferred along the movable shaft 542. The distal end 548 of the movable shaft 542 transfers the distally directed force DF to the proximal end 572 of the transition shaft 570 (FIGS. 9 and 9A). Thus, with the movable shaft 542 in the first configuration, the movable shaft 542 provides strength and pushability to the catheter 500 for delivery to the desired treatment site.

The groove 550 in the movable shaft 542 is a longitudinal groove configured such that the movable shaft 542 may be advanced or retracted over the proximal shaft 502 while providing an exit for the proximal portion of the pressure sensor wire(s) 520. While the groove 550 is desirable, it is not required. If the movable shaft 542 did not include a groove 550, when the movable shaft 542 is retracted, the portion of the pressure sensor wire(s) 520 proximal of the hub 526 would need to be at least as long as the movable shaft 542 in order to provide room for the movable shaft 542 to retract over the pressure sensor wire(s) 520 proximal of the hub 526. By providing the groove 550, the proximal portion of the pressure sensor wires(s) 520 may exit the movable shaft 542 through the groove 550 at any longitudinal position of the movable shaft 542. The moveable shaft 542 may be formed of, for example, and not by way of limitation, polyethylene, polyether block amide (PEBA, e.g. VESTAMID, PEBAX), thermoplastic elastomers (TPE), polyamide and/or combinations thereof, either blended or co-extruded, or other materials suitable for the purposes described herein. The movable shaft 542 may be selectively coupled to the hub 526 by a mechanical locking mechanism disposed with the hub 526 and actuated by a trigger, coupling mechanisms suitable for the purposes described herein. For example, and not by way of limitation, the movable shaft 542 may be selectively coupled to the hub 526 by a locking key/pin arrangement, a reversible snap fit connection, an interference fit, or other suitable couple mechanisms.

By utilizing the movable shaft 542 disposed over the proximal shaft 502, the proximal shaft 502 can have a smaller cross-sectional profile than would be required for pushability without the movable shaft 542. Thus, with the movable shaft 542 in the first configuration (FIGS. 9 and 11A), the proximal portion of the catheter 500 has a first outer diameter D5 (FIG. 11A) which is the outer diameter of the movable shaft 542. The combined strength of the proximal shaft 502 and the movable shaft 542 provides sufficient strength and pushability for the delivering the catheter 500 to the desired treatment site. Once at the desired treatment site, the movable shaft 542 may be retracted proximally and withdrawn (FIGS. 10, 10A, 10B, and 11B) such that the proximal portion of the catheter 500 has a second outer diameter D6 which is smaller than the first outer diameter D5. The second outer diameter D6 is the outer diameter of the proximal shaft 502. In one example, the second outer diameter D6 is 0.014 inch, but this is not meant to be limiting.

With an understanding of the components of catheter 500, it is now possible to describe the interactions of the various components and a method to calculate a Fractional Flow Reserve (FFR). Referring back to FIGS. 9-10, a guide catheter (not shown but similar to FIG. 1) and the guidewire 516 are advanced through the vasculature to a desired site. The guidewire 516 may be back-loaded into the catheter 500 (i.e., the proximal end of the guidewire 516 is loaded into the distal end of the guidewire lumen 514 at the distal end of distal shaft 508). The catheter 500 is in the first configuration with the movable shaft 542 disposed over the proximal shaft 502 and locked in place by the locking mechanism of the hub 526. The catheter 500 may then be advanced over the guidewire 516 and through a lumen of the guide catheter to the desired treatment site. In particular, with a distal end of the guide catheter disposed at a desired site proximal of the stenosis 902, such as in the sinus of an aortic valve, the distal shaft 508 of the catheter 500 is advanced through the lumen of the guide catheter and distal of the distal end of the guide catheter. The catheter 500 is advanced such that distal shaft 508 is disposed across the stenosis 902 of the vessel 900.

With the catheter 500 in position at the treatment site, the movable shaft 542 is removed from around the proximal shaft 502. Removing the movable shaft 542 results in the catheter 500 being in the second configuration with only the proximal shaft 502 as the proximal portion of the catheter, as shown in FIGS. 10 and 11B. With the movable shaft 542 removed, the combination of the guidewire 516 and the proximal shaft 502 occupies a smaller percentage of the lumen of the guide catheter, as shown by comparing FIG. 11B to FIG. 11A. With the catheter 500 in position and in the second configuration, the appropriate pressure measurements may be taken. Thus, blood flow adjacent the distal end of the guide catheter fills the lumen and tubing via a port in a proximal portion of the guide catheter. The proximal pressure $P_a$ at the distal end of the guide catheter is measured by an external pressure transducer via the fluid (blood) column extending through the lumen of the guide catheter and the tubing. Thus, an external pressure transducer is configured to measure the proximal or aortic (AO) pressure $P_a$ at the distal end of the guide catheter.

The external pressure transducer is configured to communicate the measured proximal pressure $P_a$ to a processor (not shown) via a pressure transducer wire, as explained above with respect to the catheter 100. However, this is not meant to limit the design and the external pressure transducer may communicate with the processor by any means suitable for the purposes described, including, but not limited to, electrical cables, optical cables, or wireless devices. Simultaneously, the pressure sensor 518 measures distal pressure $P_d$ of blood distal of the stenosis. The distal pressure $P_d$ is communicated to the processor, as explained above. The processor calculates the Fractional Flow Reserve (FFR) based on the distal pressure $P_d$ divided by the proximal/aortic pressure $P_a$, or $FFR=P_d/P_a$.

As explained above, the proximal portion of the catheter 500 with the movable shaft 542 removed has a reduced cross-sectional profile (FIG. 11B) as compared to the proximal portion of the catheter 500 with the movable shaft 542 disposed over the proximal shaft 502 (FIG. 11A). As further explained above, because the proximal or aortic pressure $P_a$ is measured using the fluid column within the lumen of the guide catheter between an outer surface of a guidewire/proximal shaft combination and an inner surface of the guide catheter, a larger profile may lead to errors in the measured proximal or aortic pressure $P_a$. Such errors are carried through to the FFR calculation noted above because the measured proximal pressure $P_a$ is used in the FFR calculation. Thus, reducing the cross-sectional profile leads to a smaller potential for error in the proximal pressure $P_a$, and hence a smaller potential for error in the FFR calculation.

Figure 12:
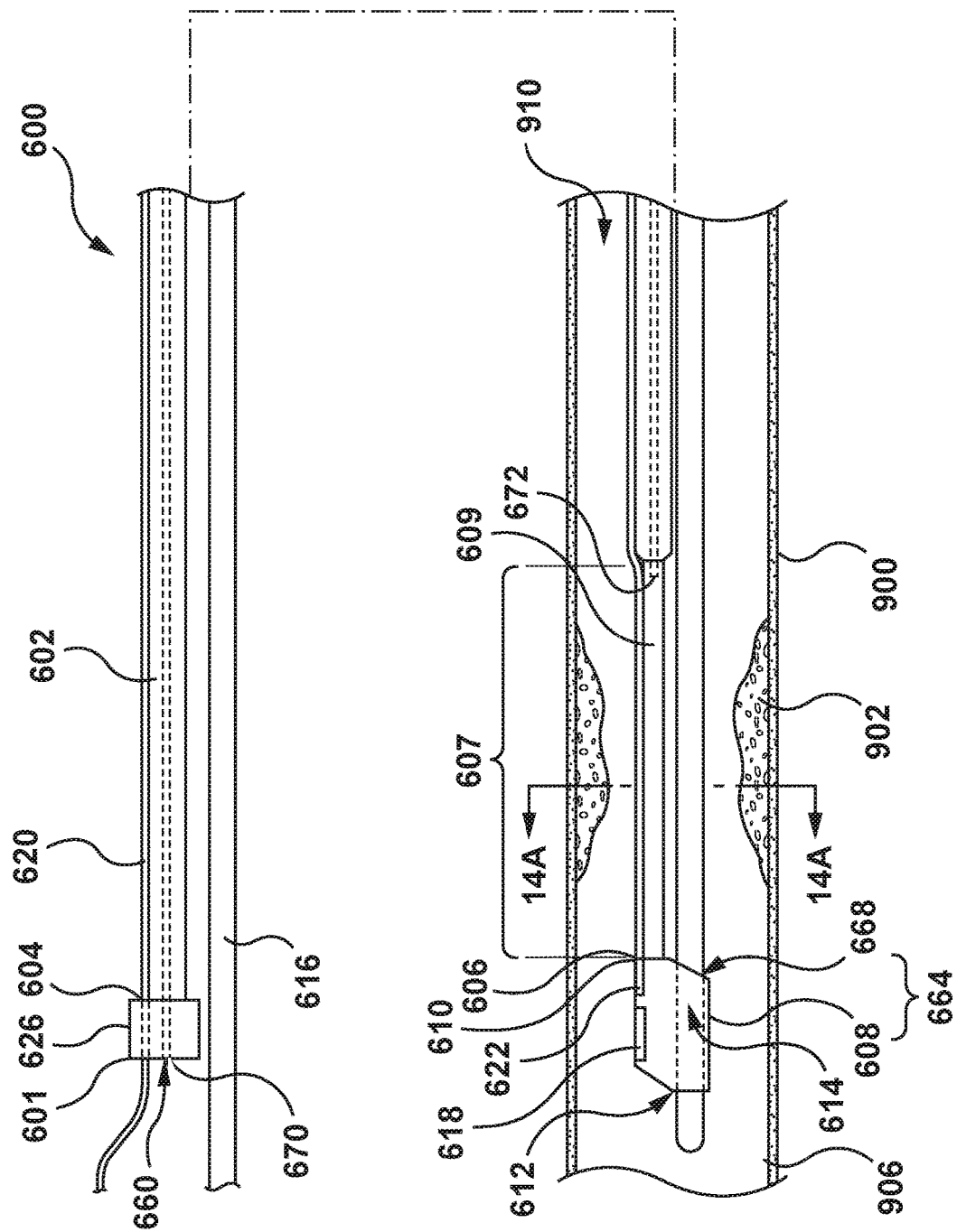
FIG. 12 is a side illustration of another embodiment of a catheter for calculating a Fractional Flow Reserve (FFR) with a distal portion of the proximal shaft in a radially expanded configuration.
Figure 13:
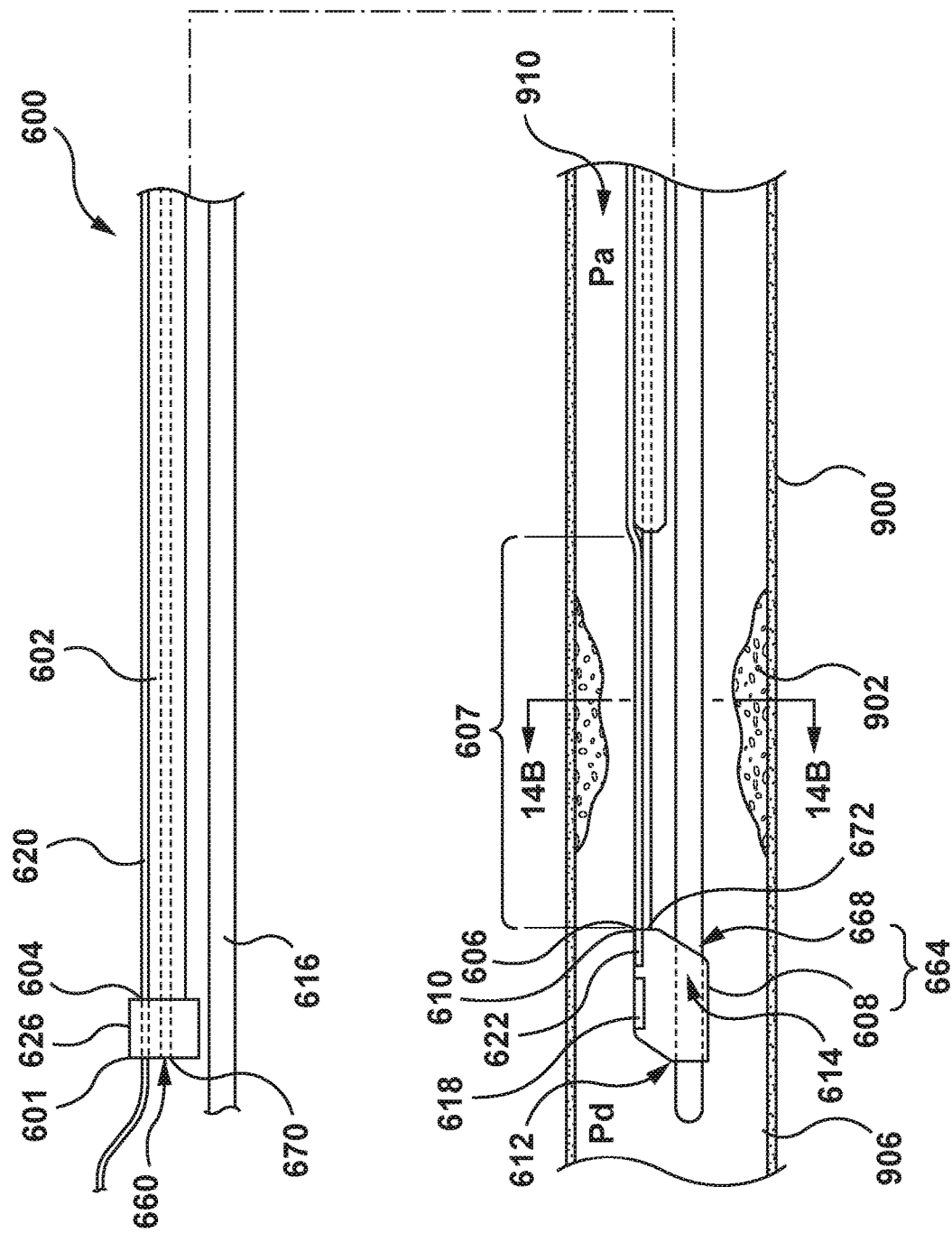
FIG. 13 is a side illustration of the catheter of FIG. 12 with the distal portion of the proximal shaft in a radially collapsed configuration.

Referring to FIGS. 12-14B, a catheter (or micro-catheter) 600 for calculating a Fractional Flow Reserve (FFR) according to another embodiment of the present disclosure is shown. The catheter 600 includes a proximal shaft 602, a distal shaft 608, a pressure sensor 618, and at least one pressure sensor wire 620, as shown in FIGS. 12-13. The pressure sensor 618 and the at least one pressure sensor wire 620 are similar to the pressure sensor 118 and the at least one pressure sensor wire 120 of the catheter 100. Therefore, details of the pressure sensor 618 and the at least one pressure sensor wire 620 will not be repeated here. The catheter 600 is configured to be disposed with a proximal portion of the proximal shaft 602 extending outside of a patient, and a distal portion of the distal shaft 608 positioned in situ within a lumen 910 of a vessel 900 having a stenosis or lesion 902. The catheter 600 is configured such that the catheter 600 measures a distal pressure $P_d$ of blood on a distal side 906 of the stenosis 902.

In an embodiment, the proximal shaft 602 of the catheter 600 is a hollow shaft including a proximal end 604 coupled a hub/handle 626, a distal end 606, and an inflation lumen 660 extending from the proximal end 604 of the proximal shaft 602 to a distal portion 607 of the proximal shaft 602. The distal portion 607 of the proximal shaft 602 is configured to extend through the stenosis 902 of the vessel 900 when the catheter 600 is positioned for measuring the distal pressure $P_d$. The distal portion 607 of the proximal shaft 602 is further configured to be radially expandable from a radially collapsed configuration (FIGS. 13 and 14B) to a radially expanded configuration (FIGS. 12 and 14A). The distal portion 607 of the proximal shaft 602 has a first outer diameter D7 when in the radially expanded configuration (FIG. 14A) and a second outer diameter D8 when in the radially collapsed configuration (FIG. 14B), with the first diameter D7 being greater than the second diameter D8. In an embodiment, the distal portion 607 of the proximal shaft 602 is formed of an elastic shape-memory material with a pre-set shape. In the embodiment of FIGS. 12-14B, the proximal shaft 602 has a pre-set shape in the radially collapsed configuration with the second outer diameter D8, as shown in FIGS. 13 and 14B. Due to the shape memory material and pre-set shape thereof, the distal portion 607 of the proximal shaft 602 of the catheter 600 actively recoils to the second outer diameter D8 after removal of the inflation fluid from the inflation lumen 660. The expandable distal portion 607 of the proximal shaft 602 may be formed as described above with respect to the proximal shafts 102, 202 of the catheters 100, 200. For example, and not by way of limitation, the distal portion 607 of the proximal shaft 602 may be formed as described in U.S. Pat. No. 9,192,751 to Macaulay et al., which is incorporated by reference herein in its entirety. The distal portion 607 of the proximal shaft 601 may be formed of material such as, but not limited to, polyether block amide (PEBA, e.g. VESTAMID, PEBAX), thermoplastic elastomers (TPE), or other materials suitable for the purposes described herein. The proximal shaft 602 may be coupled to the hub/handle 626 by adhesives, fusing, welding, or any other method suitable for the purposes of the present disclosure.

The inflation lumen 660 includes a proximal end 670 at a proximal end 601 of the catheter 600 configured to be in fluid communication with an inflation fluid source (not shown). The inflation lumen 660 extends through the proximal shaft 602 to a distal end 672 of the inflation lumen 660 in fluid communication with an interior cavity 609 of the distal portion 607 of the proximal shaft 602, as shown in FIGS. 12-13. The distal portion 607 of the proximal shaft 602 is configured to radially expand when the interior cavity 609 of the distal portion is filled with an inflation fluid, thereby transitioning to the radially expanded configuration with the first outer diameter D7 (FIGS. 12 and 14A). The distal portion 607 of the proximal shaft 602 is further configured such that as the pressure of the inflation fluid within the interior cavity 609 is reduced, the outward radial force of the inflation fluid exerted on the inner surface of the distal portion 607 decreases such that the distal portion 607 transitions to the radially collapsed configuration with the second outer diameter D8 (FIGS. 13 and 14B). When the interior cavity 609 of the distal portion 607 of the proximal shaft 602 is filled with inflation fluid such that the distal portion is in the radially expanded configuration, strength and pushability of the distal portion 607 is increased as compared to when the inflation fluid is drained from the interior cavity 609. Thus, as described in more detail below, the distal portion 607 is in the radially expanded configuration during delivery of the catheter 600 to the desired treatment site.

In an embodiment, the distal shaft 608 of the catheter 600 includes a proximal end 610 and a distal end 612. A portion of the proximal end 610 of the distal shaft 608 is coupled to a distal end 606 of the proximal shaft 602 by adhesives, fusing, welding, or any other method suitable for the purposes of the present disclosure. The distal shaft 608 further includes a guidewire lumen 614 configured to receive a guidewire 616 therein, as shown in FIGS. 12-13. The distal shaft 608 further includes a proximal guidewire exit port 668 at a proximal portion 664 of the distal shaft 608 configured to provide entry and exit of the guidewire 616 to the guidewire lumen 614. The distal shaft 608 further includes a distal guidewire exit port at the distal end 612 of the distal shaft 608. The distal shaft 608 further includes the pressure sensor 618 and a distal portion of the pressure sensor wire(s) 620. The distal portion of the pressure sensor wire(s) 620 may be disposed within a distal shaft wall 622 of the distal shaft 608. The distal shaft 608 is configured to be disposed on the distal side 906 of the stenosis 902 such that the pressure sensor 618 is disposed on the distal side 906 of stenosis 902.

With an understanding of the components of the catheter 600 above, it is now possible to describe the interactions of the various components and a method to calculate a Fractional Flow Reserve (FFR). Referring back to FIGS. 12-13, a guide catheter (not shown but as described above with respect to FIGS. 1-2) and the guidewire 616 are advanced through the vasculature to a desired site. The guidewire 616 may be back-loaded into the catheter 600 (i.e., the proximal end of the guidewire 616 is loaded into the distal end of the guidewire lumen 614 at the distal end 612 of the distal shaft 608). The catheter 600 is in the radially expanded configuration with the distal portion 607 of the proximal shaft 602 inflated. The catheter 600 may then be advanced over the guidewire 616 and through a lumen of the guide catheter to the desired treatment site. In particular, with a distal end of the guide catheter disposed at a desired site proximal of the stenosis 902, such as in the sinus of an aortic valve, the catheter 600 is advanced through the lumen of the guide catheter until the distal shaft 608 is distal of the distal end of the guide catheter and on the distal side 906 of the stenosis 902, as shown in FIG. 12.

With the catheter 600 in position at the treatment site, the inflation fluid is drained from the interior cavity 609 of the distal portion 607 of the proximal shaft 602. Thus, the distal portion 607 of the proximal shaft 602 returns to the radially collapsed configuration shown in FIGS. 13 and 14B. With the distal portion 607 of the proximal shaft 602 in the radially collapsed configuration, the combination of the guidewire 616 and the distal portion 607 occupies a smaller percentage of the vessel 900 through the stenosis 902, as shown by comparing FIG. 14B to FIG. 14A. With the catheter 600 in position and in the radially collapsed configuration, the appropriate pressure measurements may be taken. Thus, blood flow adjacent the distal end of the guide catheter fills the lumen and tubing via a port in a proximal portion of the guide catheter. The blood pressure $P_a$ at the distal end of the guide catheter is measured by an external pressure transducer via the fluid (blood) column extending through the lumen of the guide catheter and the tubing. Thus, an external pressure transducer is configured to measure proximal or aortic (AO) pressure $P_a$ at the distal end of the guide catheter.

The external pressure transducer is configured to communicate measured proximal pressure $P_a$ to a processor (not shown) via a pressure transducer wire, as explained above with respect to the catheter 100. However, this is not meant to limit the design and the external pressure transducer may communicate with the processor by any means suitable for the purposes described, including, but not limited to, electrical cables, optical cables, or wireless devices. Simultaneously, the pressure sensor 618 measures distal pressure $P_d$ of blood distal of the stenosis. The distal pressure $P_d$ is communicated to the processor, as explained above. The processor calculates the Fractional Flow Reserve (FFR) based on the distal pressure $P_d$ divided by the proximal/aortic pressure $P_a$, or $FFR=P_d/P_a$.

As explained in the Background Section above, an FFR catheter with a guidewire extending therethrough occupies a larger percentage of the vessel 900 through the stenosis 902 than a conventional FFR wire. This disrupts the blood flow through the stenosis, which can lead to a measured distal pressure $P_d$ which does not correlate to a distal pressure measured distal of the same stenosis with an FFR wire. Further, the FFR catheter needs sufficient pushability to be delivered through the vasculature to the treatment site, which may increase the size of such FFR catheters. In the embodiment of FIGS. 12-14B, the distal portion 607 of the proximal shaft 602 is inflated during delivery of the catheter 600 to the treatment site to provide sufficient pushability. Once at the treatment site, the distal portion 607 may be deflated such that the overall cross-sectional profile of the guidewire 616 and distal portion 607 in the radially collapsed configuration is equivalent to the cross-sectional profile of an FFR wire. Thus, the measured distal pressure $P_d$ is equivalent to the measured distal pressure using an FFR wire.

Referring to FIGS. 15-17B, a catheter (or micro-catheter) 700 for calculating a Fractional Flow Reserve (FFR) according to another embodiment of the present disclosure is shown. The catheter 700 includes a proximal shaft 702, a distal shaft 708, a pressure sensor 718, and at least one pressure sensor wire 720. The distal shaft 708, pressure sensor 718 and the at least one pressure sensor wire 720 are similar to the distal shaft 608, pressure sensor 118 and the at least one pressure sensor wire 120 described above with respect to the catheter 600 (regarding the distal shaft) and the catheter 100 (regarding the pressure sensor and the pressure sensor wire(s)). Therefore, details of the distal shaft 708, the pressure sensor 718, and the at least one pressure sensor wire 720 will not be repeated here. The catheter 700 is configured to be disposed with a proximal portion of the proximal shaft 702 extending outside of a patient, and a distal portion of the distal shaft 708 positioned in situ within a lumen 910 of a vessel 900 having a stenosis or lesion 902. The catheter 700 is configured to measure a distal pressure $P_d$ of blood on a distal side 906 of the stenosis 902.

Figure 15:
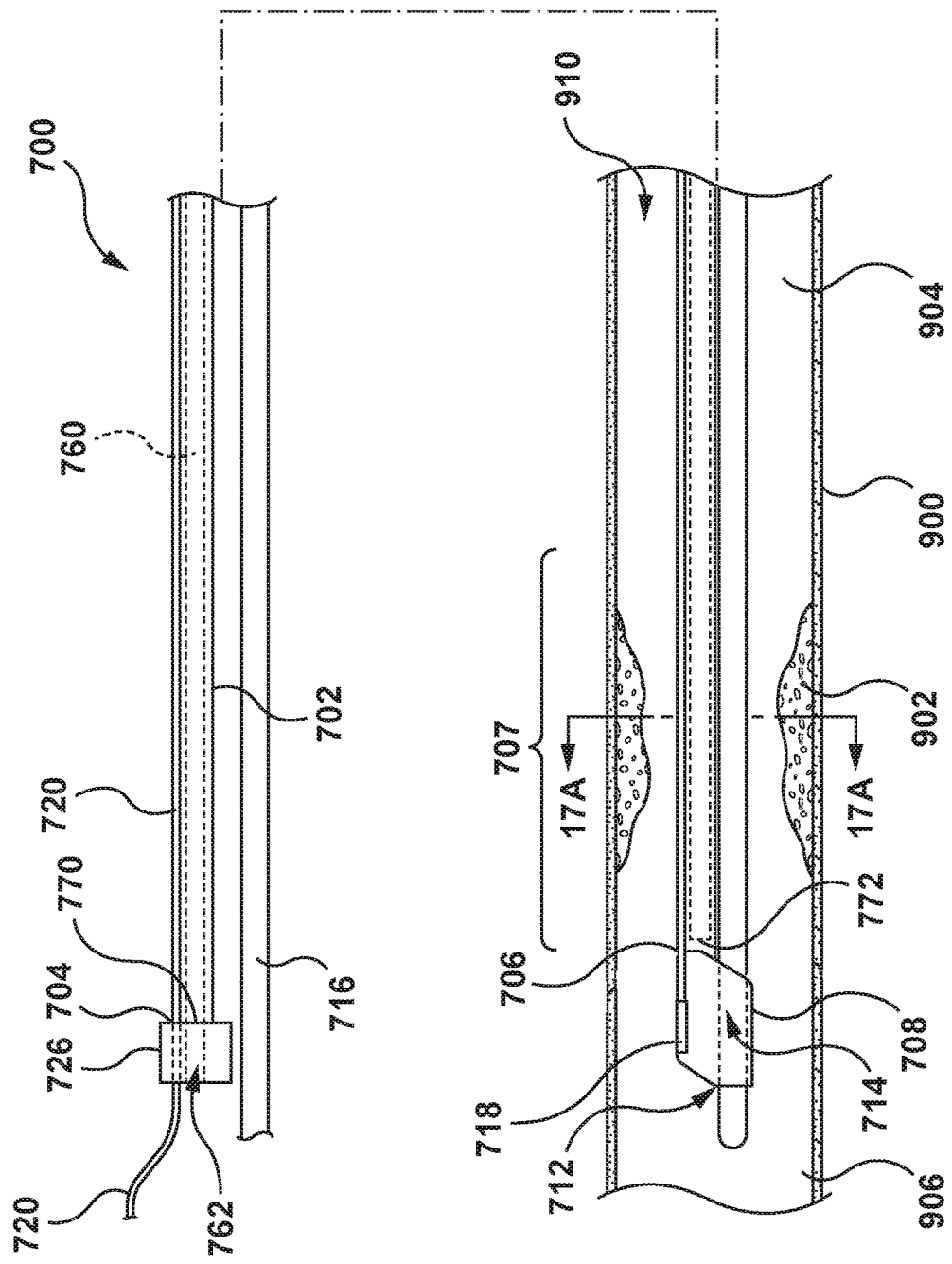
FIG. 15 is a side illustration of another embodiment of a catheter for calculating a Fractional Flow Reserve (FFR) with a distal portion of a proximal shaft in a radially expanded configuration.
Figure 16:
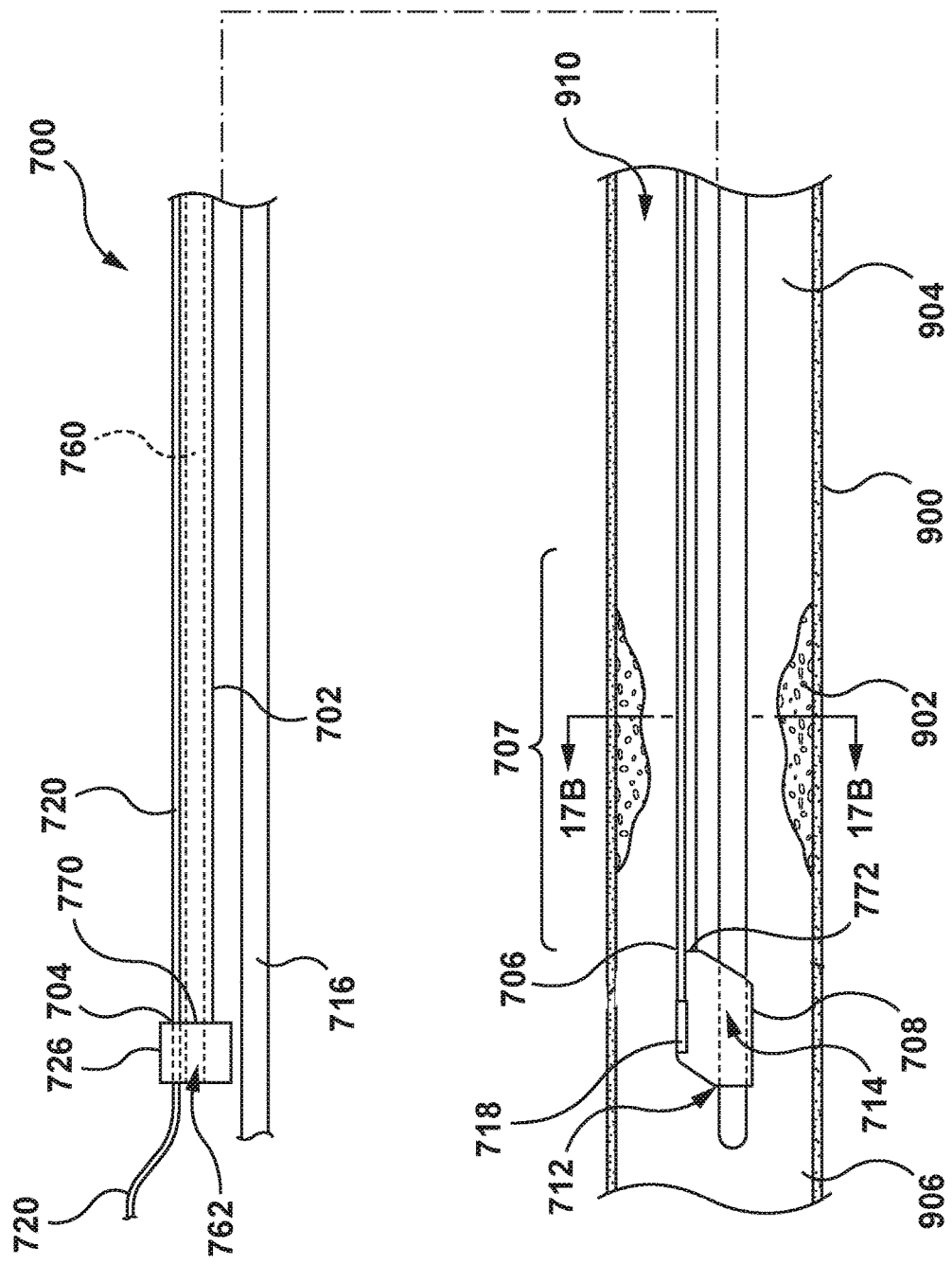
FIG. 16 is a side illustration of the catheter of FIG. 15 with the distal portion of the proximal shaft in a radially collapsed configuration.
Figure 17:
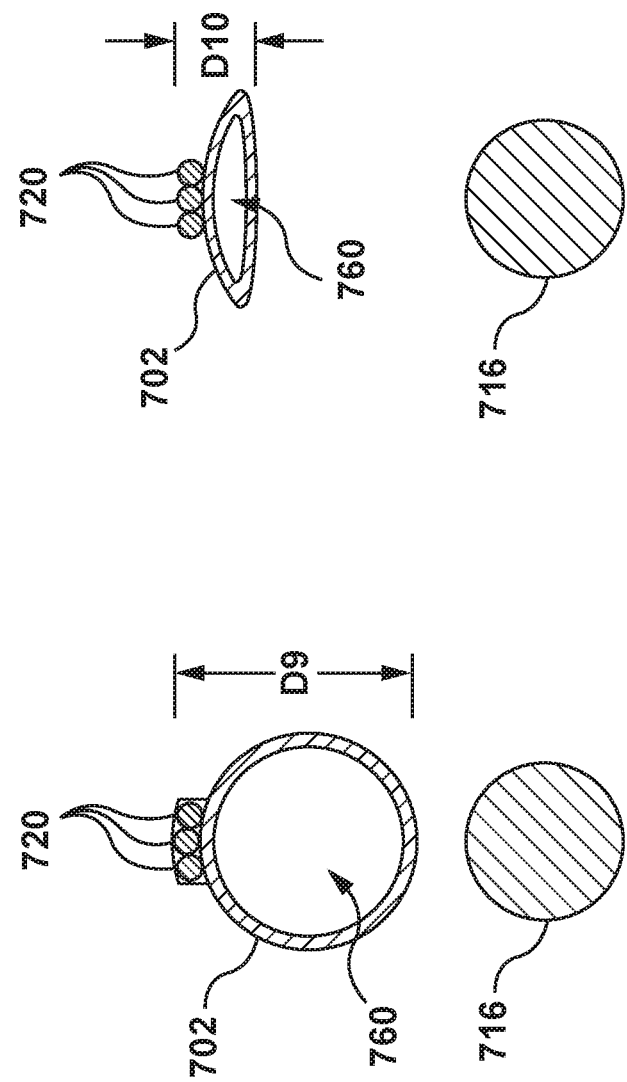
FIG. 17A is a cross-sectional illustration of an embodiment of the distal portion of the proximal shaft of the catheter of FIG. 15, taken along line 17A-17A of FIG. 15
FIG. 17B is a cross-sectional illustration of an embodiment of the distal portion of the proximal shaft of the catheter of FIG. 16, taken along line 17B-17B of FIG. 16.

The proximal shaft 702 is disposed distal of and coupled to a hub 726 by adhesives, fusing, welding, or any other method suitable for the purposes of the present disclosure. Proximal shaft 702 is a hollow shaft having a proximal end 704, and distal end 706, and an interior cavity 760. Proximal shaft 702 may be formed of an elastic shape-memory material with a pre-set shape such that proximal shaft 702 is radially expandable from a radially collapsed configuration (FIGS. 16 and 17B) to a radially expanded configuration (FIGS. 15 and 17A). The proximal shaft 702 has a first diameter D9 when in the radially expanded configuration and a second diameter D10 when in the radially collapsed configuration, with the first diameter D9 being greater than the second diameter D10, as shown in FIGS. 17A-17B. In the embodiment of FIGS. 15-17B, the proximal shaft 702 has a pre-set shape in a radially collapsed configuration with the second diameter D10, as shown in FIGS. 16 and 17B.

Due to the shape memory material and pre-set shape thereof, the proximal shaft 702 actively recoils to the radially collapsed configuration upon removal of inflation fluid from the inflation interior cavity 760. The expandable proximal shaft 702 may be formed as described above with respect to the proximal shafts 102, 202 of the catheters 100, 200. For example, and not by way of limitation, the proximal shaft 702 may be formed as described in U.S. Pat. No. 9,192,751 to Macaulay et al., which is incorporated by reference herein in its entirety. The proximal shaft 702 may be formed of, for example, and not by way of limitation, polyether block amide (PEBA, e.g. VESTAMID, PEBAX), thermoplastic elastomers (TPE), or other materials suitable for the purposes described herein.

The interior cavity 760 includes a proximal end 770 in fluid communication with an inflation fluid source (not shown) through an inflation lumen 762 disposed through the hub 726. The interior cavity 760 also includes a distal end 772 adjacent a location where the proximal shaft 702 is coupled to the distal shaft 708. The proximal shaft 702 is configured such that the inflation fluid, pumped under pressure into the interior cavity 760, fills the interior cavity 760 and exerts an outward radial force on an inner surface of the proximal shaft 702 such that the proximal shaft 702 transitions to the radially expanded configuration (FIGS. 15 and 17A). The proximal shaft 702 is further configured such that as the pressure of the inflation fluid within the interior cavity 760 is reduced, the outward radial force of the inflation fluid exerted on the inner surface of the proximal shaft 702 decreases such that the proximal shaft 702 transitions to the radially collapsed configuration (FIGS. 16 and 17B). The proximal shaft 702 with interior cavity 760 filled with inflation fluid under pressure (i.e., the radially expanded configuration) has sufficient strength and pushability for delivery of the catheter 700 to the desired treatment site.

With an understanding of the components of the catheter 700 above, it is now possible to describe the interactions of the various components and a method to calculate a Fractional Flow Reserve (FFR). Referring back to FIGS. 15-16, a guide catheter (not shown but as described above with respect to FIGS. 1-2) and the guidewire 716 are advanced through the vasculature to a desired site. The guidewire 716 may be back-loaded into the catheter 700 (i.e., the proximal end of the guidewire 716 is loaded into the distal end of the guidewire lumen 714 at the distal end 712 of the distal shaft 708). The catheter 700 is in the radially expanded configuration with the proximal shaft 702 inflated with inflation fluid. The catheter 700 may then be advanced over the guidewire 716 and through a lumen of the guide catheter to the desired treatment site. In particular, with a distal end of the guide catheter disposed at a desired site proximal of the stenosis 902, such as in the sinus of an aortic valve, the catheter 700 is advanced through the lumen of the guide catheter until the distal shaft 708 is distal of the distal end of the guide catheter and on the distal side 906 of the stenosis 902, as shown in FIG. 15.

With the catheter 700 in position at the treatment site, the inflation fluid is drained from the interior cavity 760 of the proximal shaft 702. Thus, the proximal shaft 702 returns to the radially collapsed configuration shown in FIGS. 16 and 17B. With the catheter 700 in position and the proximal shaft 702 in the radially collapsed configuration, the appropriate pressure measurements may be taken. Thus, blood flow adjacent the distal end of the guide catheter fills the lumen of the guide catheter to an external transducer via tubing and a port in a proximal portion of the guide catheter. The blood pressure $P_a$ at the distal end of the guide catheter is measured by the external pressure transducer via the fluid (blood) column extending through the lumen of the guide catheter and the tubing. Thus, the external pressure transducer is configured to measure the proximal or aortic (AO) pressure $P_a$ at the distal end of the guide catheter.

The external pressure transducer is configured to communicate measured proximal pressure $P_a$ to a processor (not shown) via a pressure transducer wire, as explained above with respect to the catheter 100. However, this is not meant to limit the design and the external pressure transducer may communicate with the processor by any means suitable for the purposes described, including, but not limited to, electrical cables, optical cables, or wireless devices. Simultaneously, the pressure sensor 718 measures distal pressure $P_d$ of blood distal of the stenosis. The distal pressure $P_d$ is communicated to the processor, as explained above. The processor calculates the Fractional Flow Reserve (FFR) based on the distal pressure $P_d$ divided by the proximal/aortic pressure $P_a$, or $FFR=P_d/P_a$.

As explained in the Background Section above, an FFR catheter with a guidewire extending therethrough occupies a larger percentage of the vessel 900 through the stenosis 902 than a conventional FFR wire. This disrupts the blood flow through the stenosis, which can lead to a measured distal pressure $P_d$ which does not correlate to a distal pressure measured distal of the same stenosis with an FFR wire. Similarly, a proximal portion of an FFR catheter with a guidewire disposed therein occupies a larger percentage of the lumen of the guide catheter, thereby possibly causing the measured proximal pressure $P_a$ to not correlate to a proximal pressure measured by an FFR wire. However, with the proximal shaft 702 in the radially collapsed configuration, the cross-sectional profile of the distal portion 707 of the proximal shaft 702 disposed through the stenosis 902 is negligible. Thus, the combined cross-sectional profile of the guidewire 716 and the distal portion 707 of the proximal shaft is equivalent to an FFR wire alone passing through the stenosis 902. Further, the cross-sectional of the proximal portion of the proximal shaft 702 extending through the lumen of the guide catheter occupies is also negligible. Thus, the cross-sectional profile if the guidewire 716 and the proximal portion of the proximal shaft 702 extending through the guide catheter is equivalent to the cross-sectional profile of an FFR wire. Therefore, FFR measured with the catheter 700 with the proximal shaft in the radially collapsed configuration is equivalent to the FFR measured with an FFR wire, thereby alleviating the need for a correction factor.

Referring to FIGS. 18-20B, a catheter (or micro-catheter) 800 for calculating a Fractional Flow Reserve (FFR) according to another embodiment of the present disclosure is shown. The catheter 800 includes a proximal shaft 802, a distal shaft 808, a pressure sensor 818, and at least one pressure sensor wire 820. The pressure sensor 818 and the at least one pressure sensor wire 820 are similar to the pressure sensor 118, and the at least one pressure sensor wire 120 described above with respect to the catheter 100. Therefore, details of the pressure sensor 818 and the at least one pressure sensor wire 820 will not be repeated here. The catheter 800 is configured to be disposed with a proximal portion of the proximal shaft 802 extending outside of a patient and a distal portion of the distal shaft 808 positioned in situ within a lumen 910 of a vessel 900 having a stenosis or lesion 902. The catheter 800 is configured to measure a distal pressure $P_d$ of blood on a distal side 906 of the stenosis 902.

In an embodiment, the proximal shaft 802 of the catheter 800 may be a hollow shaft with the pressure sensor wires(s) 820 extending through a lumen of the proximal shaft 802. In other embodiment, the proximal shaft 822 may be a solid core wire with the pressure sensor wire(s) attached to an outer surface thereof. The proximal shaft 802 includes a proximal end coupled to a handle or hub 826 and a distal end 806 coupled to the distal shaft 808. The proximal shaft 802 is configured to provide sufficient stability and pushability to advance catheter 800 to the desired treatment site.

Figure 18:
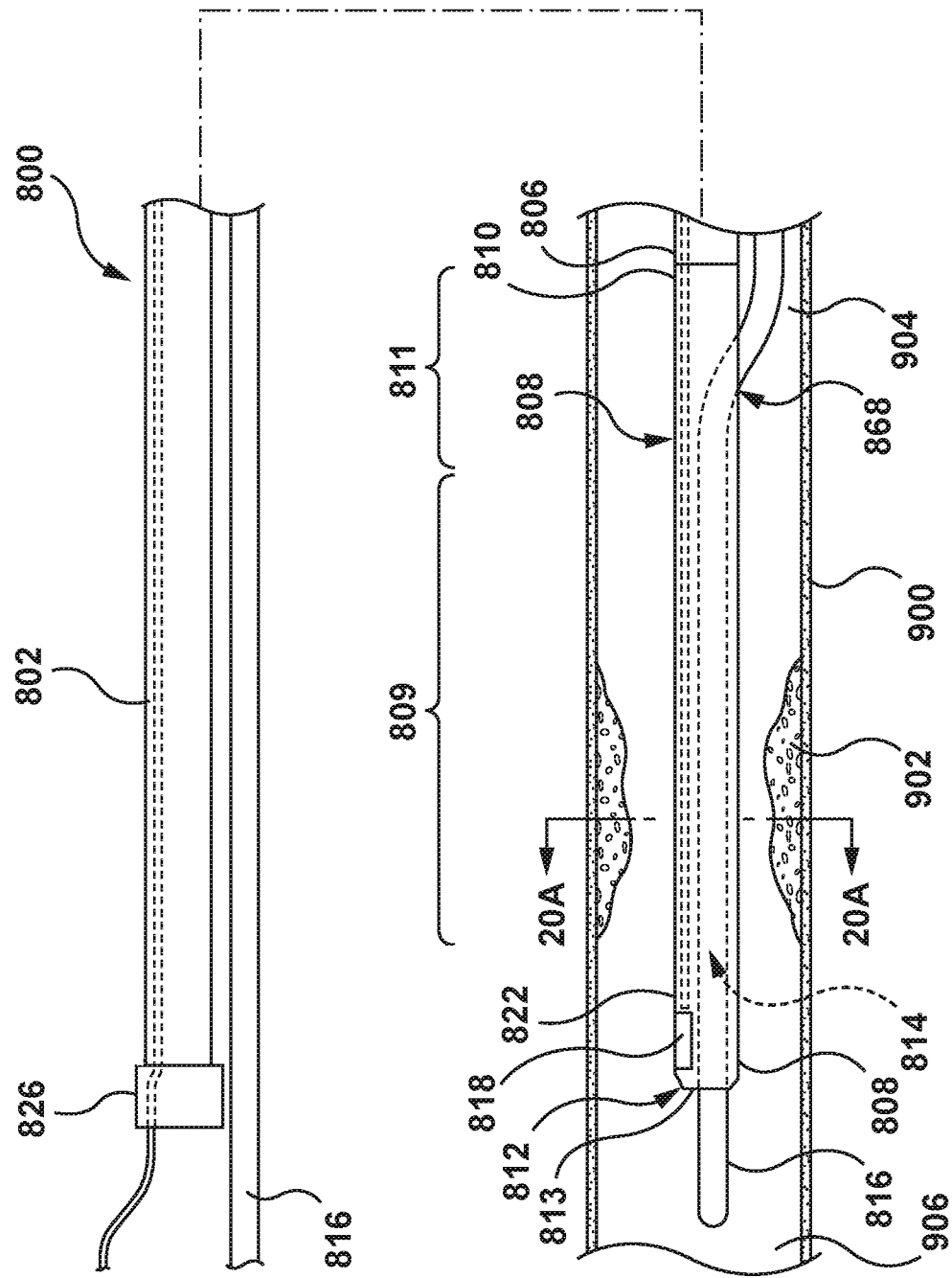
FIG. 18 is a side illustration of another embodiment of a catheter for calculating a Fractional Flow Reserve (FFR) with an expandable portion of a distal in a radially expanded configuration.
Figure 19:
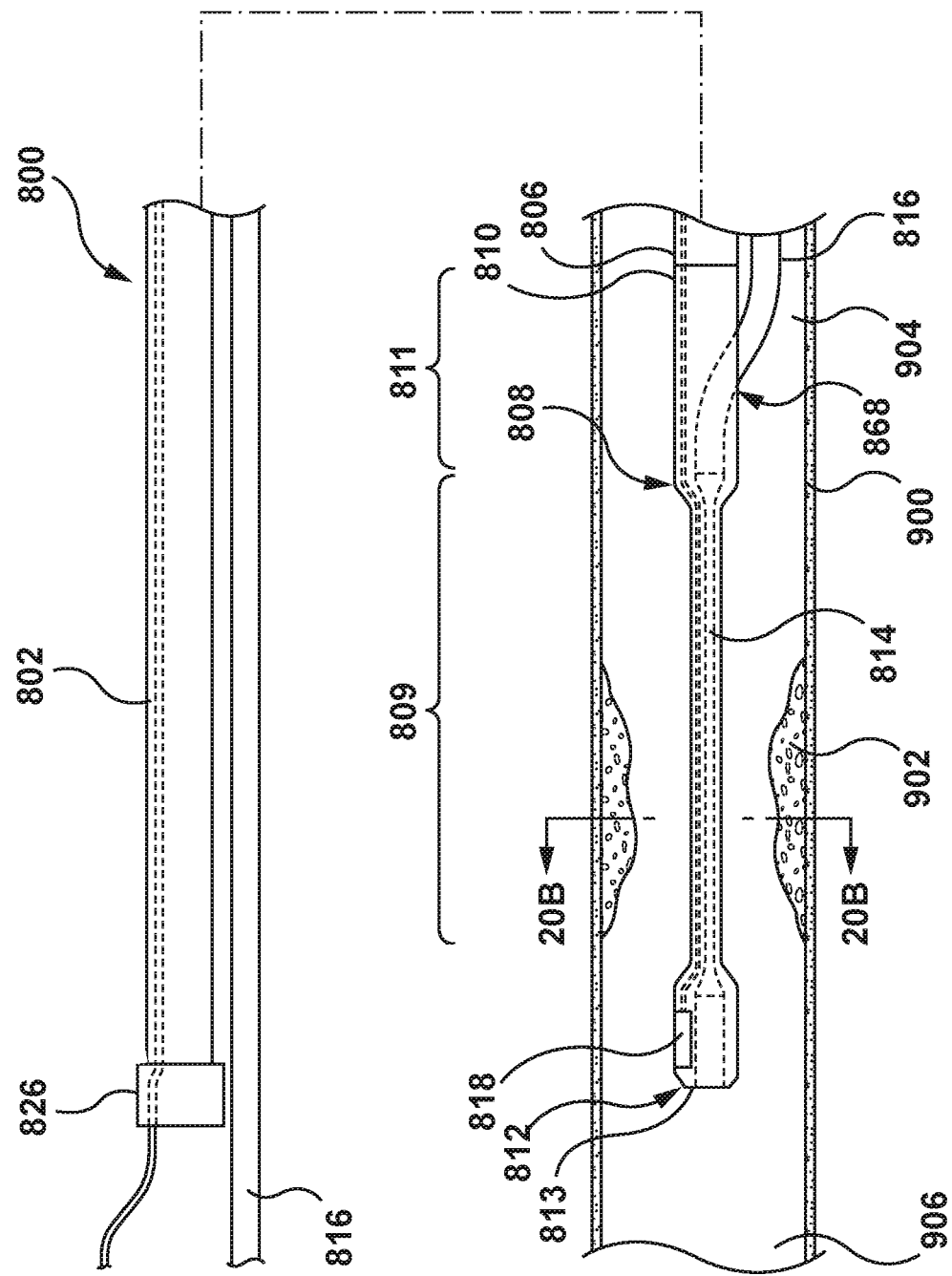
FIG. 19 is a side illustration of the catheter of FIG. 18 with the expandable portion a radially collapsed configuration.

In an embodiment, the distal shaft 808 of the catheter 800 includes a proximal end 810 coupled to the distal end 806 of the proximal shaft 802, and a distal end 812 defining a distal end of the catheter 800. As shown in FIGS. 18-19, the distal shaft 808 may be described as including a proximal or guidewire receiving portion 811, an expandable portion 809, and a distal or sensor portion 813. A guidewire lumen 814 is defined within the distal shaft 808. The guidewire lumen 814 extends distally from a guidewire port 868 in the proximal portion 811 of the distal shaft 808 to a guidewire exit port 813 at the distal end of the distal shaft 808. The guidewire lumen 814 is configured to accept a distal portion of the guidewire 816 therein, as shown in FIG. 18. The distal shaft 808 further includes the pressure sensor 818 and a distal portion of the pressure sensor wire(s) 820 disposed within a distal shaft wall 822. The distal shaft 808 is configured to be disposed on the distal side 906 of the stenosis 902 such that the pressure sensor 818 is disposed on the distal side 906 of stenosis 902. The distal shaft 808 may be coupled to the proximal shaft 802 by, for example, and not by way of limitation, adhesives, fusing, welding, for any other method suitable for the purposes of the present disclosure.

Figure 20B:
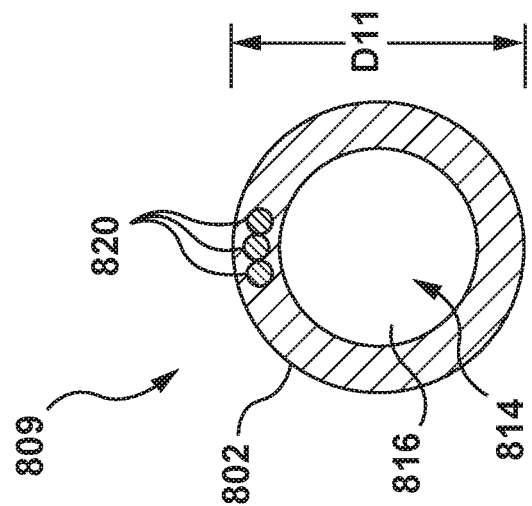
FIG. 20B is a cross-sectional illustration of an embodiment of the expandable portion of the catheter of FIG. 19, taken along line 20B-20B of FIG. 19.
Figure 20A:
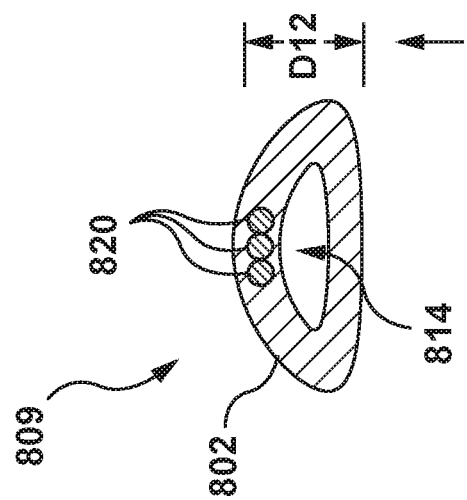
FIG. 20A is a cross-sectional illustration of an embodiment of the expandable portion of the catheter of FIG. 18, taken along line 20A-20A of FIG. 18

The expandable portion 809 of the distal shaft 808 is configured to extend through the stenosis 902 of the vessel 900 when the catheter 800 is positioned for measuring the distal pressure $P_d$ on a distal side 906 of the stenosis 902. The expandable portion 809 is expandable and collapsible such that the expandable portion 809 includes a radially expanded configuration (FIGS. 18 and 20A) and a radially collapsed configuration (FIGS. 19 and 20B). The expandable portion 809 has a first diameter D11 when in the radially expanded configuration and a second diameter D12 when in the radially collapsed configuration, with the first diameter D11 being greater than the second diameter D11, as shown in FIGS. 20A-20B. The expandable portion 809 is formed of an elastic shape-memory material with a pre-set shape. In the embodiment of FIGS. 18-20B, the expandable portion 809 has a pre-set shape in the radially collapsed configuration with the second diameter D12, as shown in FIGS. 19 and 20B. Due to the shape memory material and pre-set shape thereof, the expandable portion 809 actively recoils to the second diameter D12 upon removal of the guidewire 816 from the guidewire lumen 814. The expandable portion 809 may be formed as described above with respect to the proximal shafts 102, 202 of the catheters 100, 200. For example, and not by way of limitation, the expandable portion 809 may be formed as described in U.S. Pat. No. 9,192,751 to Macaulay et al., which is incorporated by reference herein in its entirety.

In the embodiment of FIGS. 18-20B, the guidewire 816 provides stability to the expandable portion 809 during delivery of the catheter 800 to the treatment site. Because the expandable portion 809 is near the distal end 812 of the catheter 800, less pushability is required than near the proximal end of the catheter 800. The guidewire 816 is configured to be movable within the guidewire lumen 814 of the catheter 800 as shown in FIGS. 18-19. Upon retraction of the guidewire 814 from the expandable portion 809, as shown in FIG. 19, the expandable portion 809 of the proximal shaft 802 collapses to the radially collapsed configuration, as previously described.

With an understanding of the components of the catheter 800 above, it is now possible to describe the interactions of the various components and a method to calculate a Fractional Flow Reserve (FFR). Referring back to FIGS. 18-19, a guide catheter (not shown but as described above with respect to FIGS. 1-2) and the guidewire 816 are advanced through the vasculature to a desired site. The guidewire 816 may be back-loaded into the catheter 800 (i.e., the proximal end of the guidewire 816 is loaded into the guidewire exit port 813 at the distal end of the guidewire lumen 814). As the catheter 800 is advanced over the guidewire 816, the guidewire 816 expands the expandable portion 809 to the radially expanded configuration. As the catheter 800 continues to advance over the guidewire 816, the guidewire exits the catheter 800 through guidewire port 868 proximal of the expandable portion 809. The catheter 800 is advanced over the guidewire 816 and through a lumen of the guide catheter to the desired treatment site. In particular, with a distal end of the guide catheter disposed at a desired site proximal of the stenosis 902, such as in the sinus of an aortic valve, the catheter 800 is advanced through the lumen of the guide catheter until the distal shaft 808 is distal of the distal end of the guide catheter such that the expandable portion 809 traverses the stenosis 902 and the pressure sensor 818 is on the distal side 906 of the stenosis 902, as shown in FIG. 18.

With the catheter 800 in position at the treatment site, the guidewire 816 is retracted proximally such that the guidewire 816 is proximal of the expandable portion 809 but still disposed within the guidewire lumen 814, as shown in FIG. 19. Essentially, a distal end of the guidewire 816 is disposed within the guidewire lumen 814 between the guidewire port 868 and the expandable portion 809, as shown in FIG. 19. Retraction of the guidewire from the guidewire lumen 814 of the expandable portion 809 causes the expandable portion 809 to radially collapse to the radially collapsed configuration shown in FIGS. 19 and 20B. With the catheter 800 in position and expandable portion 809 in the radially collapsed configuration, the appropriate pressure measurements may be taken. Thus, blood flow adjacent the distal end of the guide catheter fills the lumen of the guide catheter to an external transducer via tubing and a port in a proximal portion of the guide catheter. The blood pressure $P_a$ at the distal end of the guide catheter is measured by the external pressure transducer via the fluid (blood) column extending through the lumen of the guide catheter and the tubing. Thus, the external pressure transducer is configured to measure proximal, or aortic (AO) pressure $P_a$ at the distal end of the guide catheter.

The external pressure transducer is configured to communicate measured proximal pressure $P_a$ to a processor (not shown) via a pressure transducer wire, as explained above with respect to the catheter 100. However, this is not meant to limit the design and the external pressure transducer may communicate with the processor by any means suitable for the purposes described, including, but not limited to, electrical cables, optical cables, or wireless devices. Simultaneously, the pressure sensor 818 measures distal pressure $P_d$ of blood distal of the stenosis. The distal pressure $P_d$ is communicated to the processor, as explained above. The processor calculates the Fractional Flow Reserve (FFR) based on the distal pressure $P_d$ divided by the proximal/aortic pressure $P_a$, or $FFR=P_d/P_a$.

As explained in the Background Section above, an FFR catheter with a guidewire extending therethrough occupies a larger percentage of the vessel 900 through the stenosis 902 than a conventional FFR wire. This disrupts the blood flow through the stenosis, which can lead to a measured distal pressure $P_d$ which does not correlate to a distal pressure measured distal of the same stenosis with an FFR wire. In the embodiment of FIGS. 18-20B, with the expandable portion 809 in the radially collapsed configuration, the cross-sectional profile of the collapsible portion 809 disposed through the stenosis 902 is equivalent to the cross-sectional profile of an FFR wire. For example, and not by way of limitation, the second diameter D12 may be approximately 0.014 inch. Therefore, because the cross-sectional profile of the expandable portion 809 is similar to the cross-sectional profile of an FFR wire crossing the stenosis 902, the measured distal pressure $P_d$ is equivalent to the measured distal pressure using an FFR wire. Therefore, the FFR calculated using measurements taken with the catheter 800 with the expandable portion 809 in the radially collapsed configuration is equivalent to the FFR calculated using measurements taken with an FFR wire, thereby alleviating the need for a correction factor.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. For example, and not by way of limitation, the embodiments describing a radially expandable/collapsible proximal shaft may be combined with the embodiments describing a radially expandable/collapsible distal shaft. All patents and publications discussed herein are incorporated by reference herein in their entirety.

What is claimed is:

1. A catheter for measuring a fractional flow reserve, the catheter comprising:
    a shaft including a distal portion including a pressure sensor portion disposed at a distal end of the catheter and a collapsible portion extending proximally from the pressure sensor portion, the collapsible portion configured to be delivered through a stenosis in a vessel in a radially expanded configuration having a first diameter, the collapsible portion further having a radially collapsed configuration having a second diameter, wherein the first diameter is larger than the second diameter, and wherein the pressure sensor portion is not collapsible;
    a guidewire lumen configured to receive a guidewire therein disposed through the pressure sensor portion of the distal portion of the shaft; and
    a pressure sensor coupled to the pressure sensor portion of the distal portion of the shaft.

2. The catheter of claim 1, wherein the collapsible portion of the distal portion of the shaft is inflatable using an inflation fluid.

3. The catheter of claim 2, wherein the shaft includes an inflation lumen extending from a proximal end of the shaft to the collapsible portion of the distal portion of the shaft, and wherein the collapsible portion of the distal portion of the shaft includes an interior cavity in communication with the inflation lumen.

4. The catheter of claim 2, wherein the collapsible portion of the distal portion of the shaft is configured to be inflated to the radially expanded configuration during delivery of the catheter through the stenosis, and wherein the collapsible portion of the distal portion of the shaft is configured to be in the radially collapsed configuration during measurement of a distal pressure distal of the stenosis using the pressure sensor.

5. The catheter of claim 2, further comprising a guidewire exit port distal of the collapsible portion of the distal portion of the shaft.

6. The catheter of claim 1, wherein a proximal portion of the shaft is radially expandable.

7. The catheter of claim 6, wherein the proximal portion and the collapsible portion of the distal portion of the shaft are inflatable using an inflation fluid.

8. The catheter of claim 7, wherein the proximal portion and the collapsible portion of the distal portion of the shaft include an interior cavity configured to receive an inflation fluid to inflate the proximal portion and the collapsible portion of the distal portion to the radially expanded configuration.

9. The catheter of claim 1, wherein the collapsible portion of the distal portion of the shaft is formed of a shape memory material including a pre-set shape, wherein the pre-set shape is the radially collapsed configuration.

10. The catheter of claim 1, further comprising at least one pressure sensor wire operably connected to the pressure sensor, wherein the at least one pressure sensor wire extends proximally from the pressure sensor through the shaft.

11. A catheter for measuring a fractional flow reserve, the catheter comprising:
    a shaft including a distal portion, the distal portion of the shaft including a pressure sensor portion disposed at a distal end of the catheter and a collapsible portion extending proximally from the pressure sensor portion, wherein the collapsible portion includes a radially expanded configuration having a first diameter and a radially collapsed configuration having a second diameter, wherein the first diameter is larger than the second diameter;
    a guidewire lumen extending through the collapsible portion and the pressure sensor portion of the distal portion of the shaft, the guidewire lumen configured to receive a guidewire therein, wherein the collapsible portion is in the radially expanded configuration when a guidewire is disposed in the guidewire lumen of the collapsible portion, wherein the collapsible portion is in the radially collapsed configuration when the guidewire is removed from the guidewire lumen of the collapsible portion, and wherein when the guidewire is removed from the pressure sensor portion, the pressure sensor portion does not radially collapse; and
    a pressure sensor coupled to the pressure sensor portion of the distal portion of the shaft.

12. The catheter of claim 11, further comprising a guidewire port proximal of the collapsible portion and distal of a hub of the catheter, the guidewire port being in communication with the guidewire lumen, wherein in the radially expanded configuration a guidewire is disposed through the guidewire port and into the guidewire lumen and extends within the guidewire lumen through the collapsible portion and the pressure sensor portion of the distal portion of the shaft.

13. The catheter of claim 11, further comprising at least one pressure sensor wire operably connected to the pressure sensor, wherein the at least one pressure sensor wire extends proximally from the pressure sensor through the shaft.

14. The catheter of claim 11, wherein the collapsible portion of the distal portion of the shaft is configured to be in the radially expanded configuration during delivery of the catheter through a stenosis, and wherein the collapsible portion of the distal portion of the shaft is configured to be in the radially collapsed configuration during measurement of a distal pressure distal of the stenosis using the pressure sensor.

15. The catheter of claim 11, further comprising a guidewire exit port distal of the collapsible portion of the distal portion of the shaft.

16. The catheter of claim 11, wherein the collapsible portion of the distal portion of the shaft is formed of a shape memory material including a pre-set shape, wherein the pre-set shape is the radially collapsed configuration.

17. The catheter of claim 16, wherein the guidewire disposed in the collapsible portion causes the collapsible portion to expand to the radially expanded configuration and removing the guidewire from the collapsible portion causes the collapsible portion to return to the pre-set shape.

* * * * *